(12) United States Patent
Isobe et al.

(10) Patent No.: US 8,939,345 B2
(45) Date of Patent: Jan. 27, 2015

(54) REMOTE-CONTROLLED ACTUATOR

(75) Inventors: Hiroshi Isobe, Iwata (JP); Takayoshi Ozaki, Iwata (JP); Yoshitaka Nagano, Iwata (JP); Yukihiro Nishio, Iwata (JP)

(73) Assignee: NTN Corporation, Osaka (JP)

( * ) Notice: Subject to any disclaimer, the term of this patent is extended or adjusted under 35 U.S.C. 154(b) by 671 days.

(21) Appl. No.: 13/322,739

(22) PCT Filed: May 26, 2010

(86) PCT No.: PCT/JP2010/058871
§ 371 (c)(1),
(2), (4) Date: Nov. 28, 2011

(87) PCT Pub. No.: WO2010/137603
PCT Pub. Date: Dec. 2, 2010

(65) Prior Publication Data
US 2012/0067604 A1    Mar. 22, 2012

(30) Foreign Application Priority Data

May 29, 2009  (JP) .................................. 2009-130460
May 29, 2009  (JP) .................................. 2009-130461

(51) Int. Cl.
*A61B 17/04*    (2006.01)
*A61B 17/10*    (2006.01)
*A61B 17/16*    (2006.01)
*B23B 39/14*    (2006.01)
(Continued)

(52) U.S. Cl.
CPC ............. *A61B 17/1631* (2013.01); *B23B 39/14* (2013.01); *A61B 17/32002* (2013.01); *A61B 2017/00327* (2013.01)
USPC ...................................................... 227/179.1

(58) Field of Classification Search
USPC .......................... 74/490.01; 606/180; 901/28; 227/175.1–182.1
See application file for complete search history.

(56) References Cited

U.S. PATENT DOCUMENTS 2,711,724 A * 6/1955 Jenny ........................ 123/179.31
3,868,145 A * 2/1975 Cobb et al. .................... 299/37.5
(Continued)

FOREIGN PATENT DOCUMENTS

DE    10-2006-030688    4/2008
JP    60-25223           7/1985
(Continued)

OTHER PUBLICATIONS

Japanese Office Action issued Jun. 25, 2013 in corresponding Japanese Application No. 2009-130460.
(Continued)

*Primary Examiner* — Robert Long

(57) ABSTRACT

A remote controlled actuator includes an elongated spindle guide section (3), a distal end member (2) fitted to the distal end thereof for alteration in attitude, and a drive unit housing (4a) connected with a base end of the spindle guide section (3). The distal end member (2) rotatably support a spindle (13) holding a tool (1). The spindle guide section (3) includes a rotary shaft (22) for transmitting a rotation of the spindle (13) and an attitude altering member (31) for altering the attitude of the distal end member (2) both within an outer shell pipe (25) forming an outer shell. The attitude altering member (31) is reciprocally movably inserted in a guide pipe (30) within the outer shell pipe (25). A guide pipe restraining unit (50) is provided for restraining the guide pipe (30) from moving within the outer shell pipe (25).

12 Claims, 18 Drawing Sheets

(51) Int. Cl.
*A61B 17/32* (2006.01)
*A61B 17/00* (2006.01)

(56) References Cited

U.S. PATENT DOCUMENTS

| | | | | |
|---|---|---|---|---|
| 3,869,003 | A * | 3/1975 | Yamada et al. | 175/171 |
| 3,888,317 | A * | 6/1975 | Walters | 173/193 |
| 4,141,255 | A * | 2/1979 | Nilsson | 74/25 |
| 4,265,231 | A | 5/1981 | Scheller, Jr. et al. | |
| 4,299,529 | A * | 11/1981 | Inaba et al. | 414/590 |
| 4,465,425 | A * | 8/1984 | Schwappach | 414/685 |
| 4,466,429 | A | 8/1984 | Loscher et al. | |
| 4,483,562 | A * | 11/1984 | Schoolman | 294/104 |
| 4,517,853 | A * | 5/1985 | Tani et al. | 74/89.32 |
| 4,751,821 | A * | 6/1988 | Birchard | 60/698 |
| 4,787,262 | A * | 11/1988 | Kozawa et al. | 74/490.06 |
| 5,002,543 | A * | 3/1991 | Bradshaw et al. | 606/62 |
| 5,405,344 | A | 4/1995 | Williamson et al. | 606/1 |
| 5,431,323 | A * | 7/1995 | Smith et al. | 227/177.1 |
| 5,702,408 | A * | 12/1997 | Wales et al. | 606/139 |
| 5,738,481 | A * | 4/1998 | Rogers | 414/744.6 |
| 6,193,709 | B1 | 2/2001 | Miyawaki et al. | |
| 7,104,072 | B2 * | 9/2006 | Thompson | 60/786 |
| 7,326,209 | B2 | 2/2008 | Kidooka | |
| 7,717,653 | B2 * | 5/2010 | Miyata et al. | 408/127 |
| 7,842,028 | B2 * | 11/2010 | Lee | 606/1 |
| 7,944,554 | B2 | 5/2011 | Horiuchi et al. | |
| 8,393,242 | B2 * | 3/2013 | Ozaki et al. | 74/479.01 |
| 8,511,195 | B2 * | 8/2013 | Isobe et al. | 74/490.01 |
| 8,602,125 | B2 * | 12/2013 | King | 173/221 |
| 8,663,253 | B2 * | 3/2014 | Saliman | 606/145 |
| 2004/0019352 | A1 | 1/2004 | Kidooka | |
| 2004/0138529 | A1 * | 7/2004 | Wiltshire et al. | 600/144 |
| 2007/0265653 | A1 | 11/2007 | Suzuki | |
| 2009/0262354 | A1 | 10/2009 | Horiuchi et al. | |
| 2010/0012340 | A1 * | 1/2010 | Kuosmanen | 173/184 |
| 2011/0100659 | A1 * | 5/2011 | Murate et al. | 173/104 |
| 2011/0179894 | A1 | 7/2011 | Isobe et al. | |
| 2013/0023900 | A1 * | 1/2013 | Nishio et al. | 606/130 |
| 2013/0184863 | A1 * | 7/2013 | Isobe et al. | 700/245 |
| 2013/0233583 | A1 * | 9/2013 | Nishio et al. | 173/44 |

FOREIGN PATENT DOCUMENTS

| | | |
|---|---|---|
| JP | 6-11936 | 2/1994 |
| JP | 2000-271132 | 10/2000 |
| JP | 2000-296134 | 10/2000 |
| JP | 2001-017446 | 1/2001 |
| JP | 2002-543870 | 12/2002 |
| JP | 2004-057454 | 2/2004 |
| JP | 2005-528159 | 9/2005 |
| JP | 2007-301149 | 11/2007 |
| JP | 2007-315798 | 12/2007 |
| JP | 2009-73381 | 4/2009 |
| WO | WO 00/67650 | 11/2000 |
| WO | WO 03/101308 A1 | 12/2003 |
| WO | WO 2010/041397 A1 | 4/2010 |

OTHER PUBLICATIONS

Japanese Office Action issued Jun. 25, 2013 in corresponding Japanese Application No. 2009-130461.

International Search Report for PCT/JP2010/058871 mailed Aug. 3, 2010.

International Preliminary Report on Patentability mailed Dec. 22, 2011 issued in corresponding International Patent Application No. PCT/JP2010/058871.

* cited by examiner

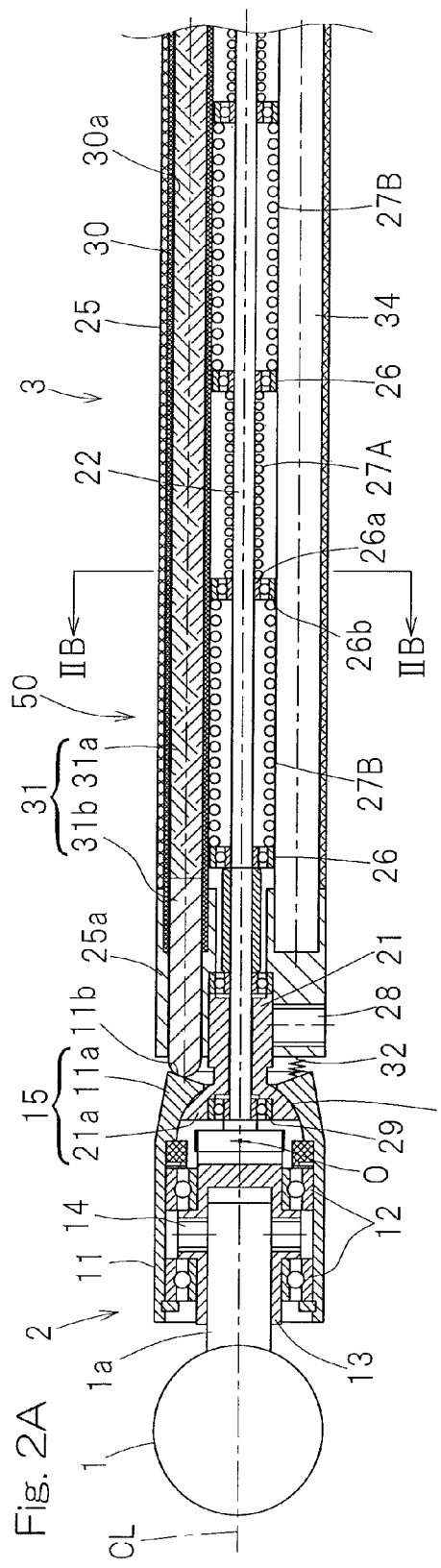
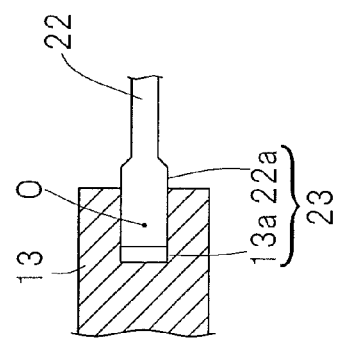
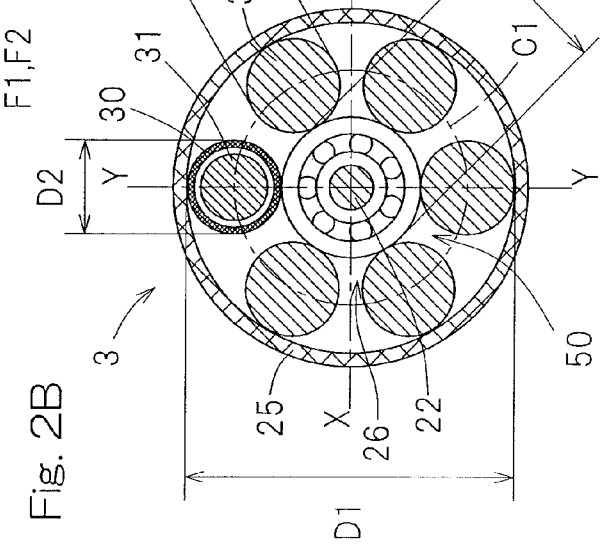

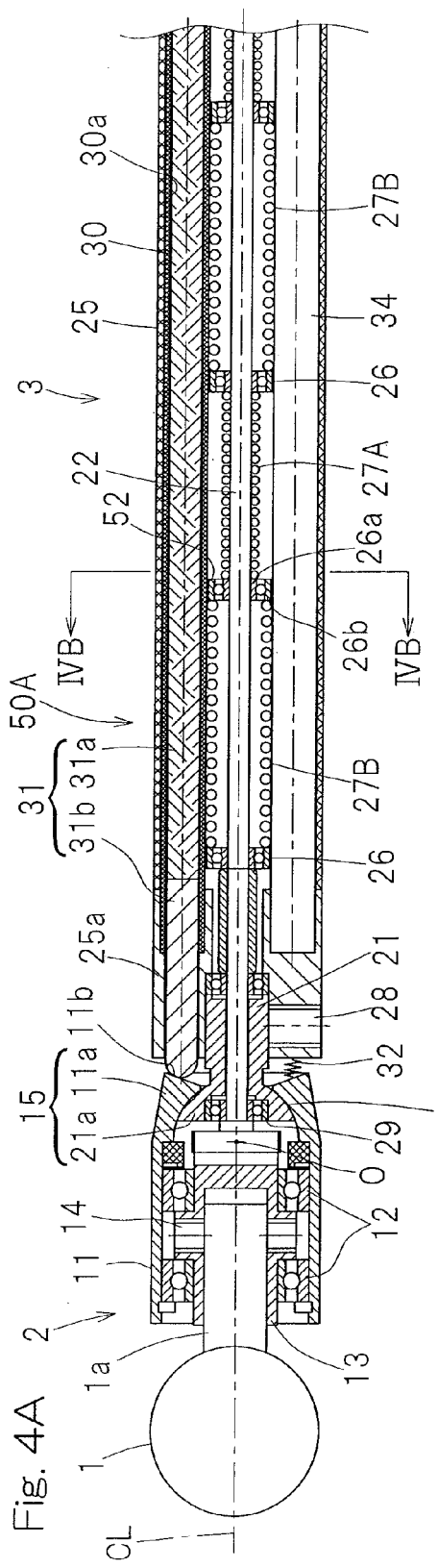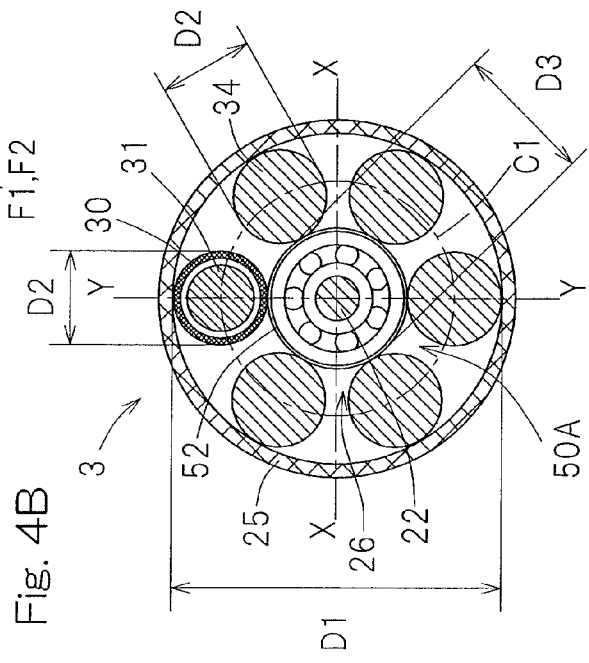

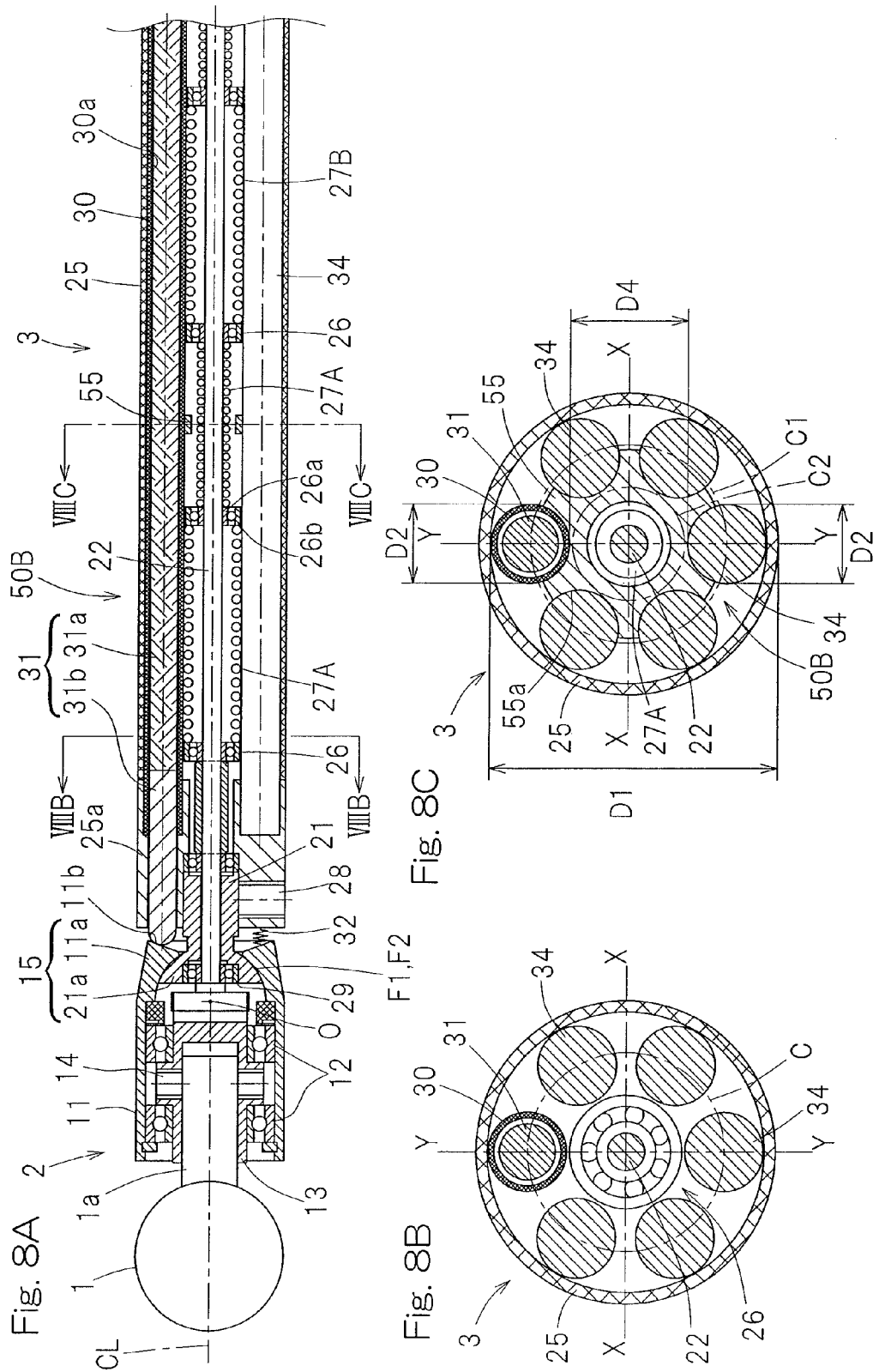

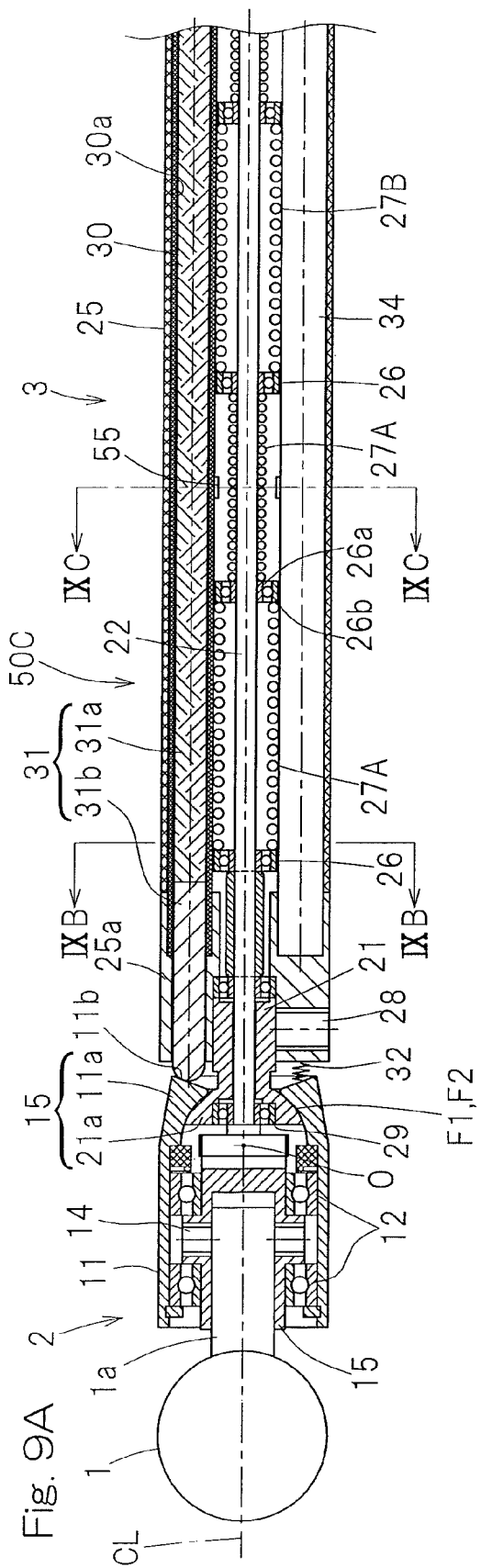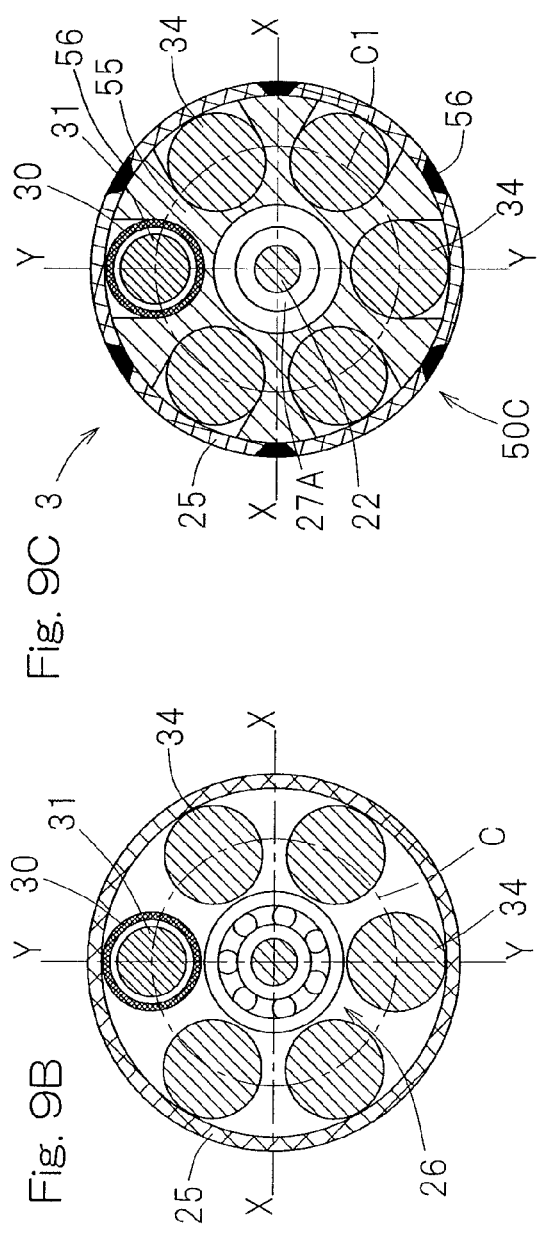

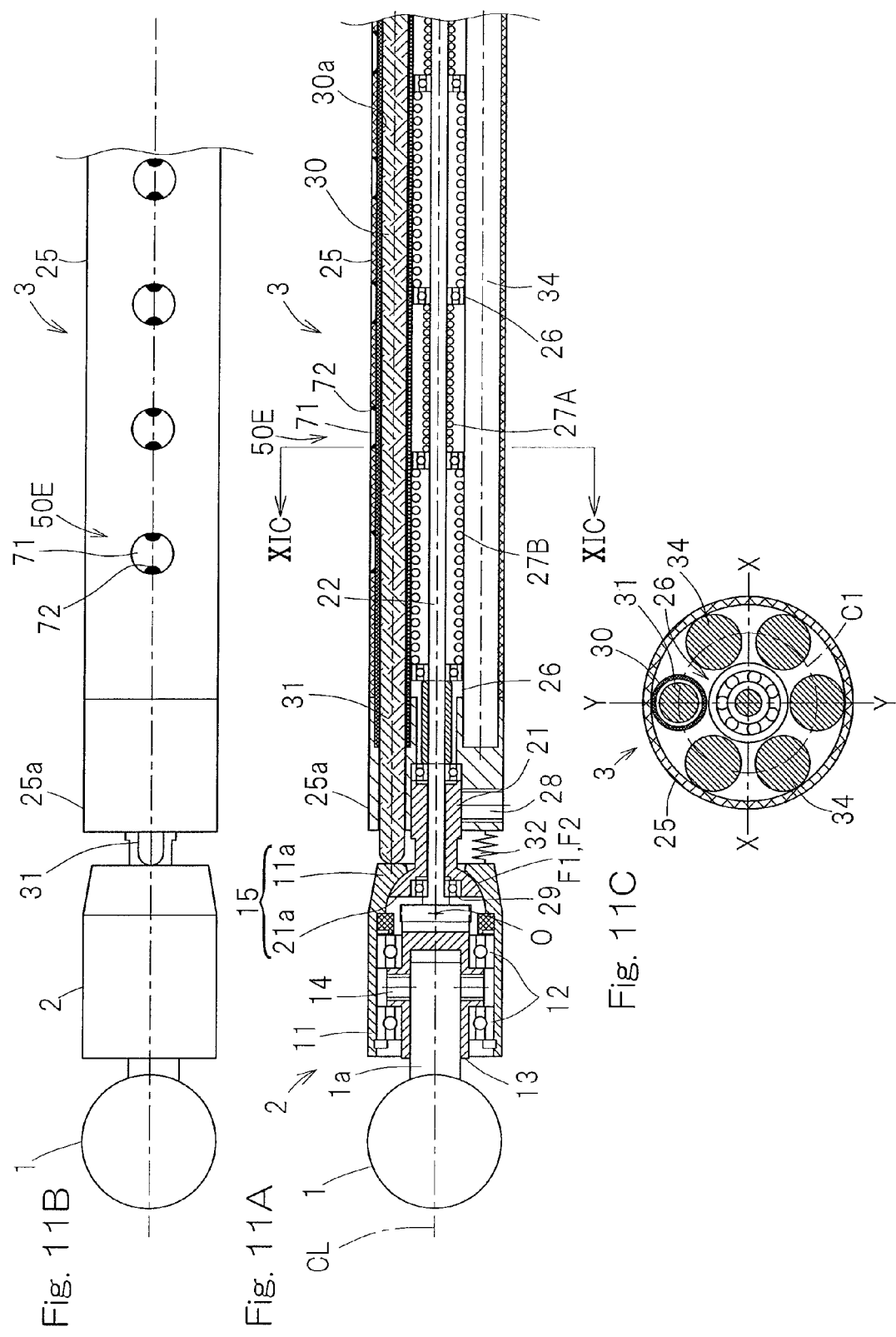

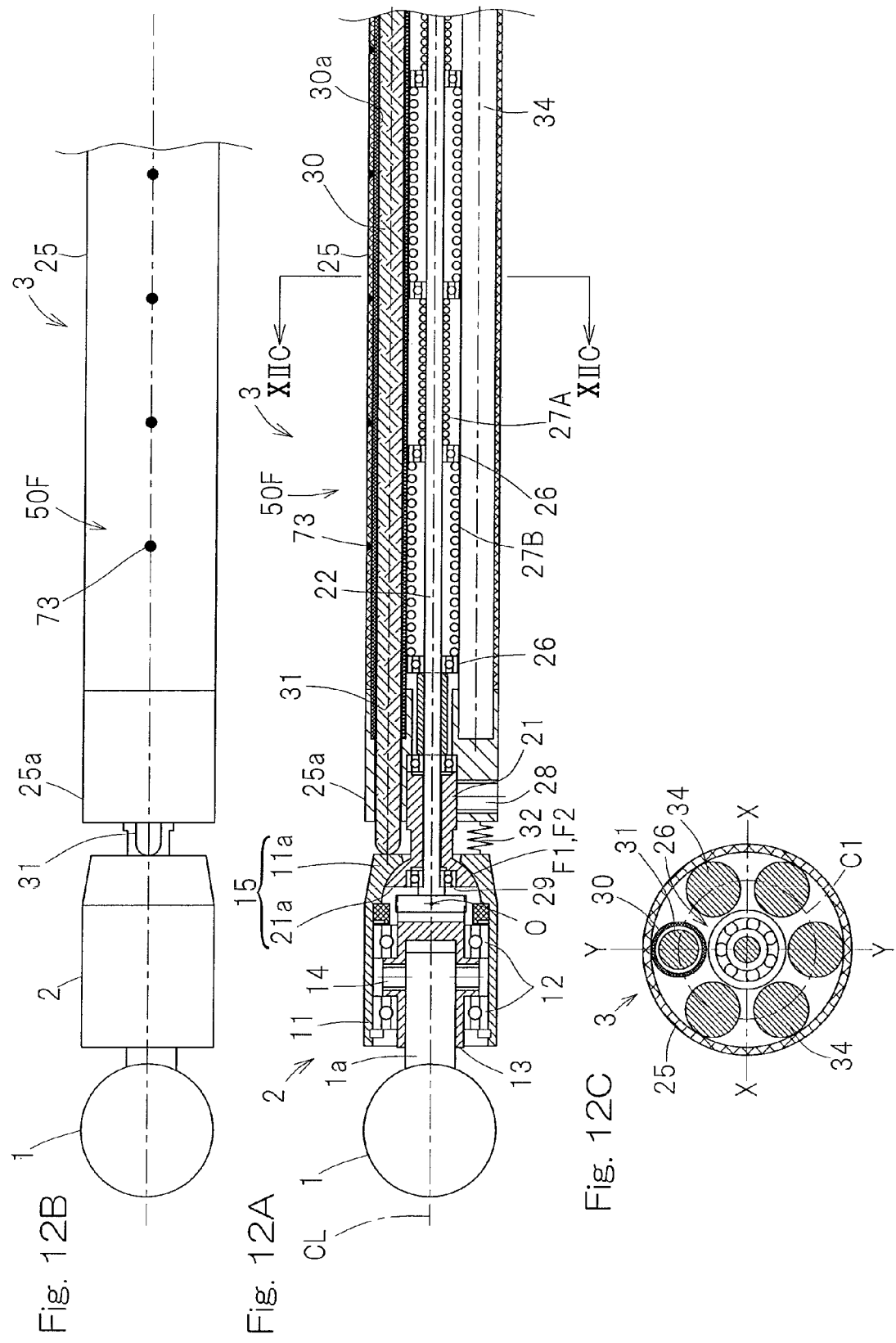

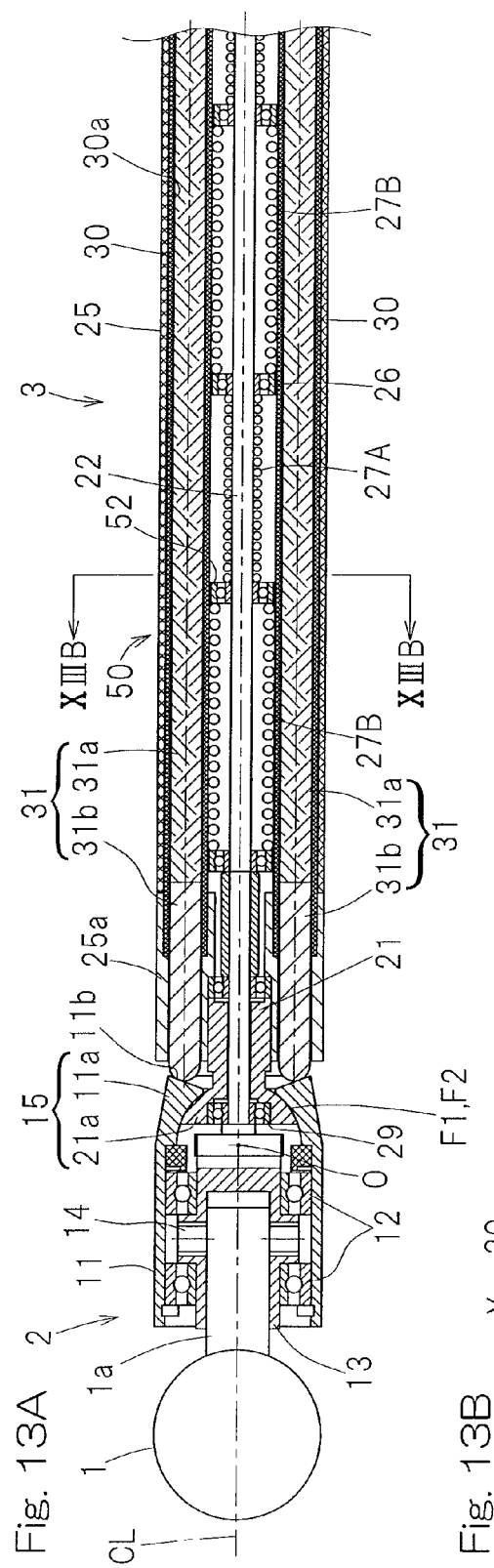
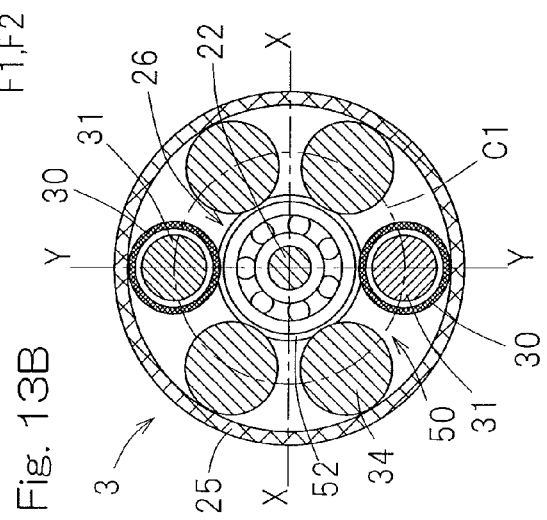
Fig. 13A
Fig. 13B

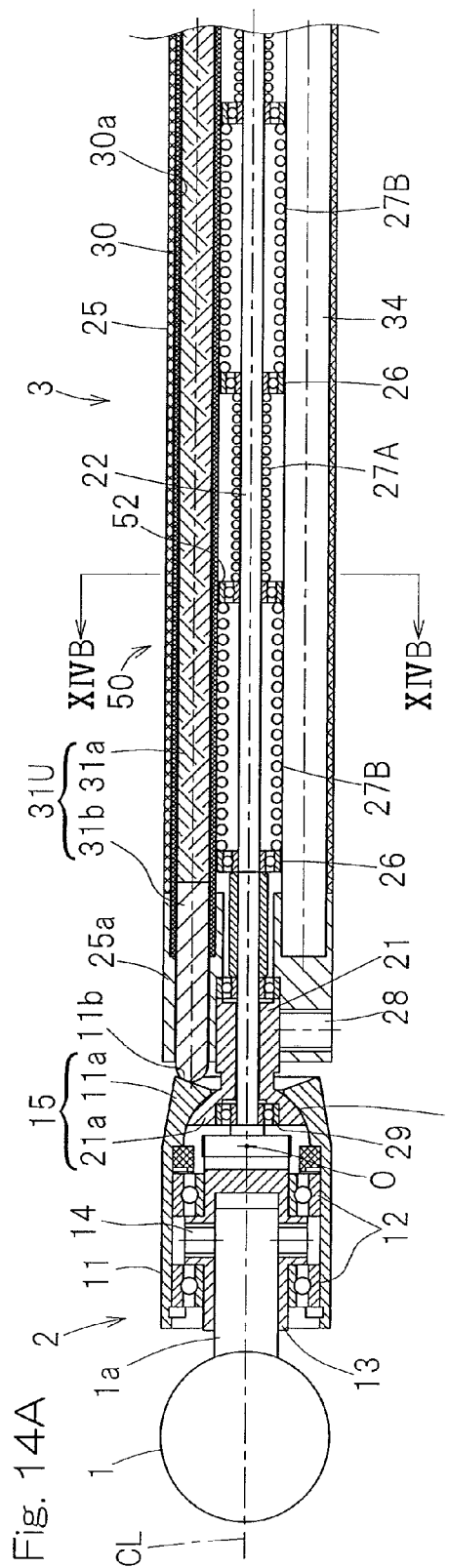
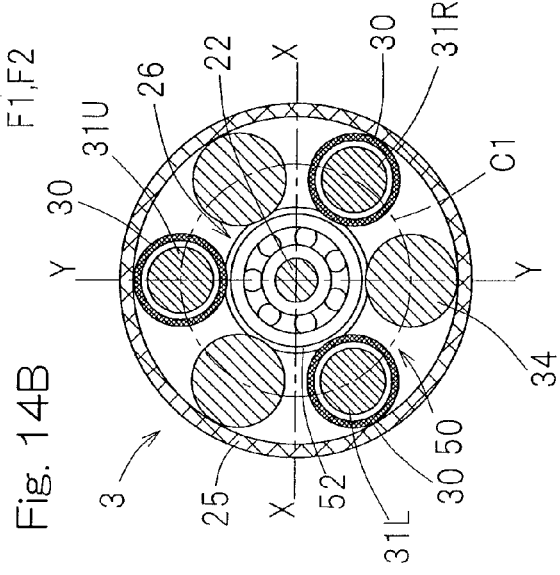
Fig. 14A
Fig. 14B

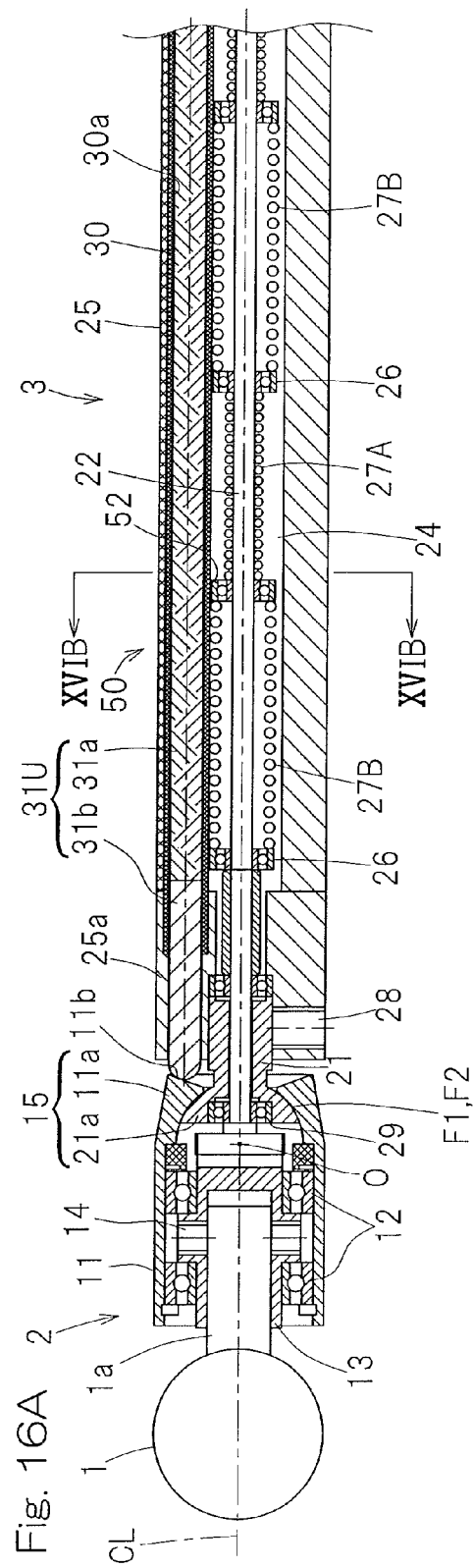
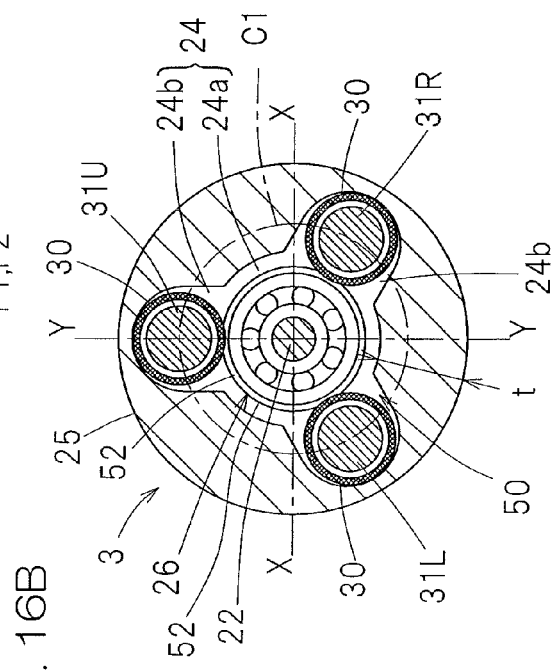
Fig. 16A
Fig. 16B

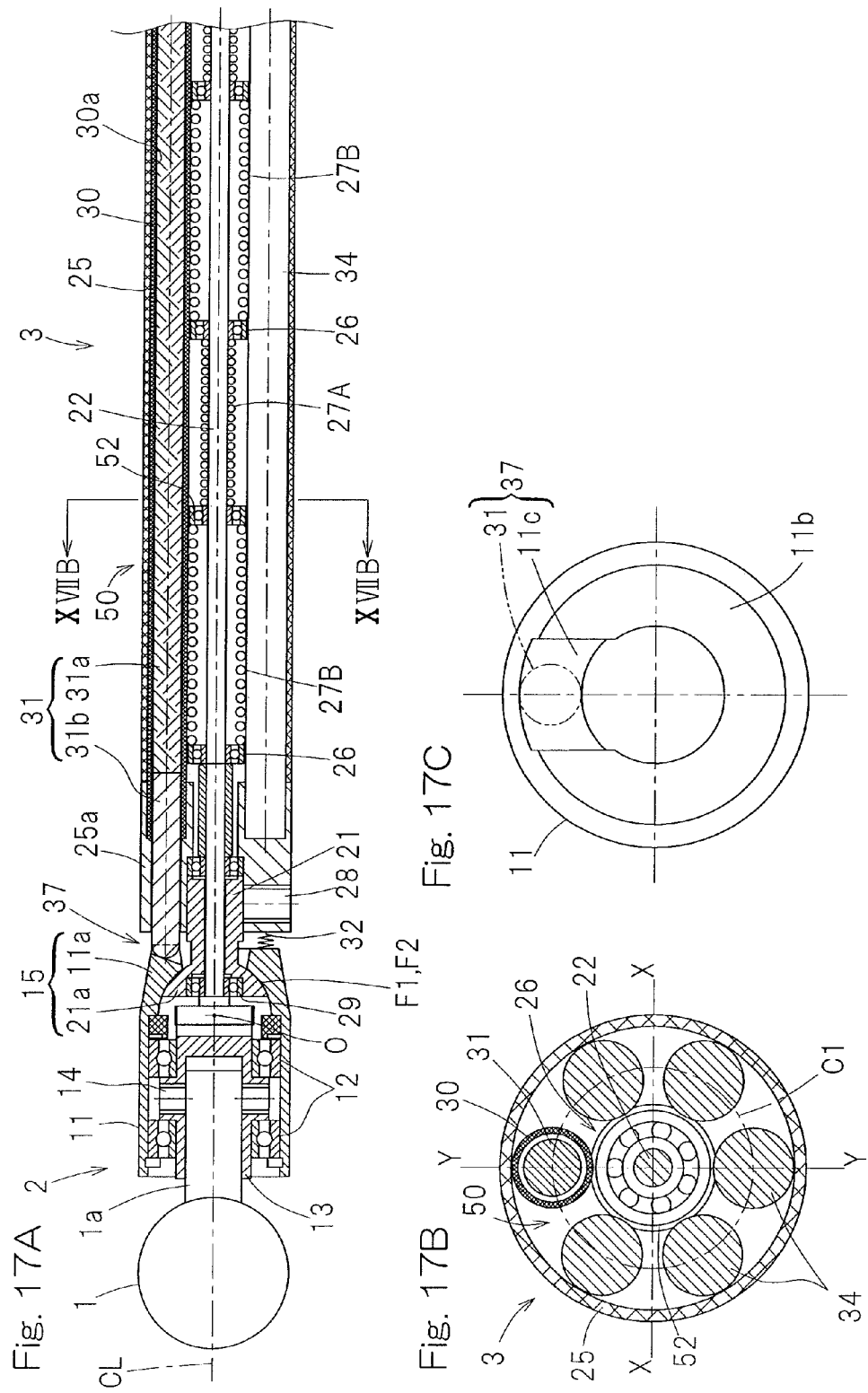

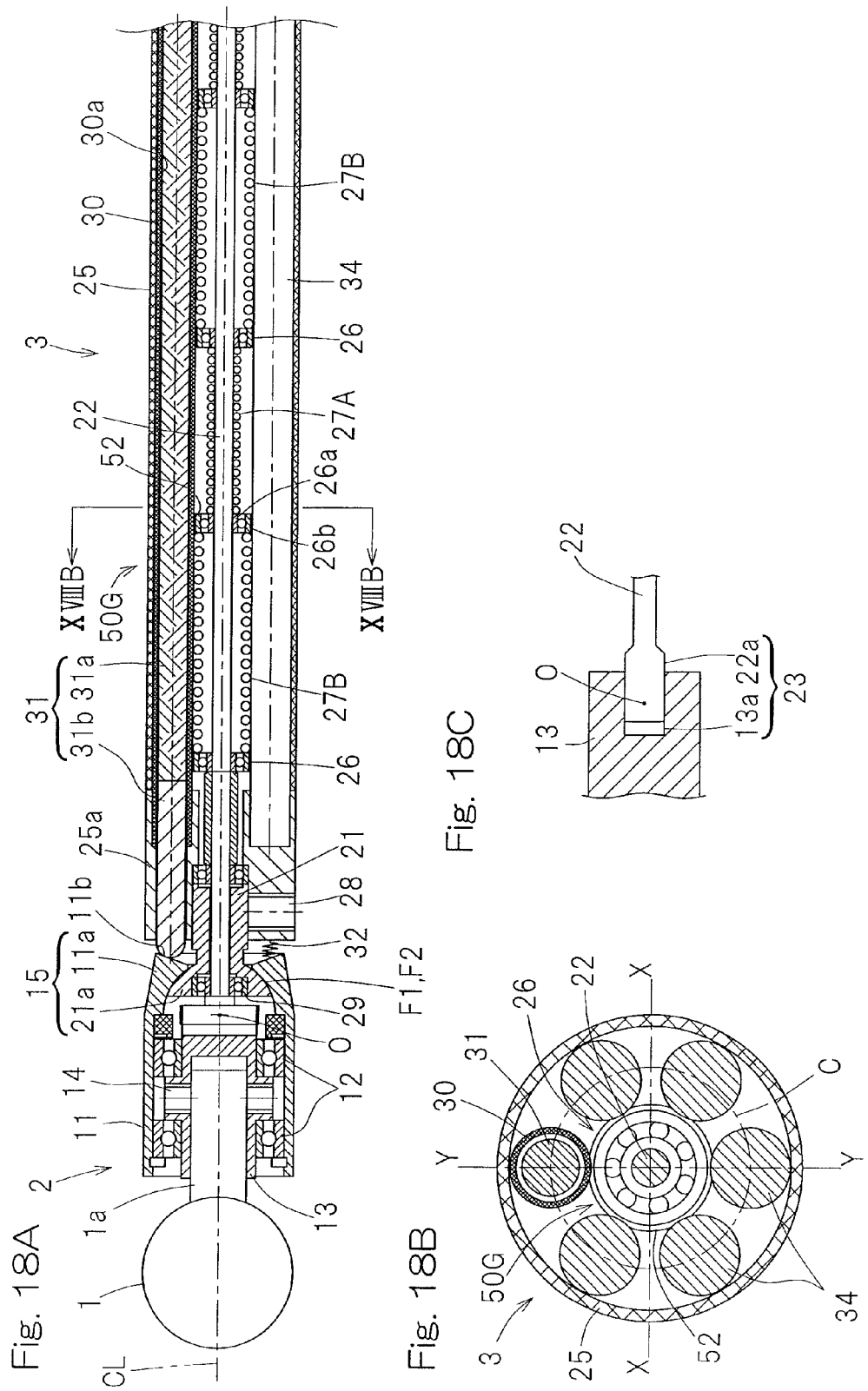

REMOTE-CONTROLLED ACTUATOR

CROSS REFERENCE TO RELATED APPLICATIONS

This application claims the benefit under 35 U.S.C. Section 371, of PCT International Application No. PCT/JP2010/058871, filed May 26, 2010, which claimed priority to Japanese Application Nos. 2009-130460 and 2009-130461, filed May 29, 2009 in the Japanese Patent Office, the disclosures of which are hereby incorporated by reference.

BACKGROUND OF THE INVENTION

1. Field of the Invention

The present invention relates to a remote controlled actuator for use in medical and machine processing fields and capable of changing the attitude of a machine tool.

2. Description of Related Art

Remote controlled actuators are currently available; some are used in the medical field for osteal treatment and some are used in the mechanical processing field for drilling and cutting. Any of those remote controlled actuators controls by remote control a machine tool fitted to a distal end of an elongated pipe of a linear or curved configuration. However, since the conventional remote controlled actuator is designed solely to control only the rotation of the machine tool by remote control, difficulties have been encountered in processing of a complicated shape and processing at a site difficult to view with eyes from the outside in the medical field. Also, in the drilling process, the capability of processing not only the linear line, but also the curved configuration is often required. In addition, in the cutting process, the capability is required to perform the process at a site deep in grooves. In the following description, conventional art and problems inherent in the remote controlled actuator will be discussed with reference to the medical field.

In the orthopedic field, the artificial joint replacement is well known, in which a joint, of which bone has been abraded by due to bone deterioration, is replaced with an artificial joint. The joint replacement surgery requires a living bone of a patient to be processed to enable an artificial joint to be implanted. In order to enhance the strength of postoperative adhesion between the living bone and the artificial joint, such processing is required to be performed precisely and accurately in conformity to the shape of the artificial joint.

By way of example, during the hip joint replacement surgery, a thigh bone is opened to secure access of an artificial joint into the femoral marrow cavity. In order to secure a strength of contact between the artificial joint and the bone, surfaces of contact of the artificial joint and the bore must be large and so the opening for insertion of the artificial joint is processed to represent an elongated shape extending deep into the bone. As a medical actuator used in cutting the bone in a manner described above, the actuator is known, in which a tool is rotatably provided in a distal end of an elongated pipe and, on the other hand, a drive source such as, for example, a motor is mounted on a proximal end of the pipe so that the tool can be driven through a rotary shaft disposed inside the elongated pipe. (See, for example, the Patent Document 1 listed below.) Since in this type of medical actuator a rotatable element that is exposed bare to the outside is only the tool at the distal end of the elongated pipe, the tool can be inserted deep into the bone.

The surgical operation for artificial joint replacement generally accompanies skin incision and muscular scission. In other words, the human body must be invaded. In order to minimize the postoperative trace, it is quite often desirable that the elongated pipe referred to above is not necessarily straight, but is moderately curved. To meet this desire, the following technique has hitherto been suggested. For example, the Patent Document 2 listed below discloses the elongated pipe having its intermediate portion curved twice to displace an axial position of the distal end of the pipe relative to the longitudinal axis of the proximal end of the same pipe. To make the axial position of the distal end of the pipe relative to the longitudinal axis of the proximal end of the same pipe is also known from other publications. Also, the Patent Document 3 listed below discloses the elongated pipe rotated by 180°.

PRIOR ART LITERATURE

[Patent Document 1] JP Laid-open Patent Publication No. 2007-301149
[Patent Document 2] U.S. Pat. No. 4,466,429
[Patent Document 3] U.S. Pat. No. 4,265,231
[Patent Document 4] JP Laid-open Patent Publication No. 2001-17446

If in a condition, in which the artificial joint is inserted into an artificial joint insertion hole formed in the living bone, a large gap exists between the living bone and the artificial joint, a large length of time is required to accomplish the postoperative adhesion between the living bone and the artificial joint and, therefore, it is considered desirable that the gap should be as small as possible. Also, it is important that respective surfaces of contact between the living bone and the artificial joint be smooth, and accordingly, a high precision is required in processing the artificial joint insertion hole. Whatever shape the pipe takes, the working range of the tool is limited by the shape of the pipe and, therefore, it is difficult to process the artificial joint insertion hole so that the living bone and the artificial joint may have smooth contact surfaces and, yet, the gap between the living bone and the artificial joint may be small while skin incision and muscular scission are minimized at the same time.

In general, it is quite often that the patient's bone, where an artificial joint is to be implanted, exhibits a strength lowered as a result of aging and, in a certain case, the bone itself is deformed. Accordingly, the processing of the artificial joint insertion hole is more difficult to achieve than generally considered.

In view of the foregoing, the applicant or assignee of the present invention has attempted to provide a remote controlled actuator of a type, in which the attitude of the tool coupled to the distal end can be changed by remote control so that the processing of the artificial joint insertion hole can be relatively easily and accurately performed. This is because if the attitude of the tool can be changed, the tool can be maintained at a proper attitude regardless of the shape of the pipe and, hence, the meticulous processing can be performed. It has, however, been found that since the tool is connected to the distal end of the elongated pipe, disposition of a mechanism for changing the attitude of the tool is considerably limited and, therefore, artifices are required to overcome those limitations. It is to be noted that in the case of the medical actuator having no elongated pipe used therein, a portion where the tool is mounted can change its attitude relative to a portion to be gripped by hand (See, for example, Patent Document 4 listed above.), but nothing has yet been suggested in the art that the attitude of the tool can be altered by remote control.

Even though the attitude of the tool can be altered by remote control, an accurate positioning of a distal end position of the tool is required. However, if the attitude of the tool is made alterable by remote control, it comes that a rotary shaft for transmitting a rotation to the tool and an attitude altering member for altering the attitude of the tool should be provided within the pipe section and, hence, the structure of the pipe section becomes so complicated that element that affects the positioning accuracy of the tool may increase.

Also, in order to finish the surface to be cut beautifully, it is necessary to perform the processing with the tool driven at a high speed. In order to accomplish this, the rotary shaft for transmitting the rotation to the tool must be driven at a high speed. However, since a mechanism for altering the attitude of the tool is also provided within the elongated pipe section accommodating therein the rotary shaft, the structure tends to become complicated. Accordingly, it has been desired that the rotary shaft be functionally and compactly accommodated within the pipe section and that the pipe section must have a structure good for the assemblability and mass-productivity.

The present invention has for its object to provide a remote controlled actuator, in which the attitude of the tool provided at a distal end of the elongated pipe section can be altered by remote control, the distal end position of the tool can be accurately positioned and the processing accuracy is high. Another object of the present invention is to provide the remote controlled actuator of the type referred to above, in which the rotary shaft can be supported within the pipe section affordably enough to permit the tool to be driven at a high speed, and in which the rotary shaft for transmitting the rotation to the tool is so functionally and compactly accommodated within the pipe section enough to exhibit a good assemblability and mass-productivity of the pipe section.

A remote controlled actuator which includes a spindle guide section of an elongated configuration, a distal end member fitted to a tip end of the spindle guide section through a distal end member connecting unit for alteration in attitude, and a drive unit housing to which a base end of the spindle guide section is connected. The distal end member rotatably supports a spindle for holding a tool. The spindle guide section includes a rotary shaft for transmitting rotation of a tool rotating drive source, provided within the drive unit housing, to the spindle, a guide hole so as to extend to opposite ends thereof, and an attitude altering member reciprocally movably inserted within the guide hole for altering the attitude of the distal end member. The attitude altering member is, while a tip end thereof is held in contact with the distal end member, selectively advanced or retracted one at a time. An attitude altering drive source for selectively advancing or retracting the attitude altering member is provided within the drive unit housing. The remote controlled actuator further includes an outer shell pipe defining an outer shell for the spindle guide section, a guide pipe positioned within the outer shell pipe having an inner diametric hole defining the guide hole, and a guide pipe restraining unit for restraining the guide pipe from moving within the outer shell pipe.

According to the above described construction, as a result of rotation of the tool fitted to the distal end member, cutting of the bone or the like takes place. In such case, when the attitude altering member is selectively advanced and retracted one at a time by the attitude altering drive source, the tip end of the attitude altering member works on the distal end member to allow the attitude of the distal end member, fitted to the tip end of the spindle guide section through the distal end member connecting unit for alteration in attitude, to alter. The attitude altering drive source is provided within the drive unit housing on the base end side of the spindle guide section and the alteration of the attitude of the distal end member is carried out by remote control. Since the attitude altering member is passed through the guide hole, the attitude altering member can work on the distal end member properly at all time without being displaced in a direction transverse to the longitudinal direction thereof, and the operation to alter the attitude of the distal end member takes place accurately.

The provision of the guide pipe restraining unit for restraining the guide pipe from moving within the outer shell pipe results in an increase of the rigidity of the guide pipe. Accordingly, a displacement or force of the attitude altering drive source provided in the drive unit housing can be accurately transmitted to the distal end member and, therefore, the positioning accuracy of the tool increases. If the guide pipe moves within the outer shell pipe, the displacement or force of the attitude altering drive source gets away in a direction radially of the guide pipe at the time such displacement or force is transmitted to the distal end member through the attitude altering member within the guide pipe. Therefore, the displacement or force of the attitude altering drive source will not be accurately transmitted to the distal end member, resulting in worsening of the positioning accuracy of the tool. In the present invention, however, since the movement of the guide pipe such as discussed above is restrained by the guide pipe restraining unit, the positioning accuracy of the tool increases.

In the present invention, the guide pipe restraining unit may be operable to urge the guide pipe against an inner diametric surface of the outer shell pipe. When the guide pipe is brought into engagement with an inner diametric surface of the outer shell pipe by the guide pipe restraining unit, a gap between the guide pipe and the outer shell pipe diminishes and the guide pipe will become hard to move within the outer shell pipe. Also, due to the friction between respective contact surfaces of the guide pipe and the outer shell pipe, the guide pipe will become hard to move.

Where the rotary shaft support member for rotatably supporting the rotary shaft is employed, the guide pipe restraining unit may be operable to urge the guide pipe against the inner diametric surface of the outer shell pipe by adjusting at least one or more of an inner diametric dimension of the outer shell pipe, an outer diametric dimension of the guide pipe and an outer diametric dimension of the rotary shaft support member. By adjusting the at least one or more of the dimensions of the various component parts referred to above, the guide pipe can press the inner diametric surface of the outer shell pipe. Since this structure does not require a high dimensional accuracy of each of the various components, it can be manufactured at a low cost.

In the present invention, where the rotary shaft is positioned at a center of the outer shell pipe, a plurality of the guide pipe or at least one guide pipe, and an arbitrarily chosen number of members (hereinafter referred to as "identical outer diametric members") each having an outer diameter, which is the same as that of the guide pipe, are arranged in a circumferential direction in a juxtaposed fashion relative to each other, arrangement may be made such that a relationship as $D1 \leq D2 \times 2 + D3$ can establish, wherein $D1$ represents an inner diametric dimension of the outer shell pipe, $D2$ represents an outer diametric dimension of the identical outer diametric member and the guide pipe, and $D3$ represents an outer diametric dimension of the rotary shaft support member. In other words, when no gap exist or a negative gap is provided between the outer shell pipe, and the guide pipe or the identical outer diametric members, nor between the guide pipe or the outer diametric members and the rotary shaft support member, both of the guide pipe and the identical outer diametric member are urged against the inner diametric surface of the outer shell pipe and also against an outer diametric surface of the rotary shaft support member. For this reason, the guide pipe and the identical outer diametric members are restrained from moving within the outer shell pipe in a direction radially of the outer shell pipe. Also, even by the friction taking place between the respective contact surfaces of both of the guide pipe and the identical outer diametric members and between both of the outer shell pipe and the rotary shaft support member, the guide pipe and the identical outer diametric members become hard to move. Accordingly, the rigidity of the guide pipe can be increased.

In the present invention, a plurality of rotary shaft support members for rotatably supporting the rotary shaft may also be provided, in which case the guide pipe restraining unit may include a guide pipe contact member provided between at least one set of the neighboring rotary shaft support members to contact the guide pipe. Even when the guide pipe contact member that contacts the guide pipe is provided between at least one set of the neighboring rotary shaft support members, movement of the guide pipe within the outer shell pipe can be restrained.

The guide pipe contact member referred to above may function to urge the guide pipe against an inner diametric surface of the outer shell pipe. When the guide pipe is urged against the inner diametric surface of the outer shell pipe by means of the guide pipe contact member, the gap between the guide pipe and the outer shell pipe is eliminated and, therefore, the guide pipe becomes hard to move within the outer shell pipe. Also, because of the friction taking place between the respective contact surfaces of the guide pipe and the outer shell pipe, the guide pipe becomes hard to move.

Where each of the rotary shaft support member is rolling bearings and a spring element is provided between the neighboring rolling bearings for applying a preload to the neighboring rolling bearings, it is desirable that the guide pipe contact member is provided at an axial location where the spring element is disposed on a side of an inner ring of each of the rolling bearings. In the event that the spring element is provided between the neighboring rolling bearings, interference between the spring element and the guide pipe contact member can be avoided when the guide pipe contact member is provided at the axial location where the spring element is disposed on the side of the inner ring of each of the rolling bearings.

In the present invention, there may be further provided a rotary shaft support member for rotatably supporting the rotary shaft within the spindle guide section, and a fixing and supporting member for supporting the rotary shaft support member in a fixed condition, in which case the guide pipe restraining unit is made up of a gap adjusting member for adjusting a gap dimension between the rotary shaft support member and the fixing and supporting member.

According to the above construction, since the use is made of the rotary shaft support member for rotatably supporting the rotary shaft within the spindle guide section, the rotation of the tool rotation drive source can be transmitted to the spindle by driving the rotary shaft at a high speed. For this reason, the processing can be performed with the tool driven at a high speed and the surface to be cut can be finished beautifully. Since the rotary shaft support member is supported in the fixed condition by the fixing and supporting member, vibration of the rotary shaft can be suppressed and an undesirable impairment to the rotary shaft and/or the rotary shaft support member can be avoided. Also, since the vibration of the actuator in its entirety can be minimized during the use, the operability thereof increases and the noise is reduced.

Also, since the use is made of the gap adjusting member for adjusting the gap dimension between the rotary shaft support member and the fixing and supporting member, it can accommodate the difference in gap dimension resulting from the manufacturing accuracy or the like and the rotary shaft support member can be assuredly supported by the fixing and supporting member in the fixed condition. Also, whatever shape the spindle guide section may take, the rotary shaft support member can be assuredly supported by the fixing and supporting member in the fixed condition to suit thereto and, hence, an excellent assemblability and an excellent mass-productivity can be obtained. By way of example, where no gap adjusting unit is employed, in the case of the spindle guide section of the linear shape, the large gap dimension between the rotary shaft support member and the fixing and supporting member prevents the fixing and supporting member from firmly supporting the rotary shaft support member, and thus, vibration of the rotary shaft is considerable. As a result, it may occur that the rotary shaft and/or the rotary shaft support member may be damaged and vibration and noise during the use will become considerable. In the case of the spindle guide section of the curved shape, the assemblability will be adversely affected if the gap is small. The use of the gap adjusting unit is effective to resolve those problems as discussed above.

In the present invention, it is possible for the gap adjusting member to be made up of an elastic member provided on an outer periphery of the rotary shaft support member. If the gap adjusting member is made up of the elastic member, deformation of the elastic member occurs in dependence on the size of the gap between the rotary shaft support member and the fixing and supporting member and, therefore, the rotary shaft member can be stably supported at all times. Also, if the gap adjusting member is made up of the elastic member, vibration of the rotary shaft is absorbed by the elastic member and, hence, the vibration of the rotary shaft is reduced.

Where the gap adjusting member is made up of the elastic member as described above, the rotary shaft support member may be a rolling bearing including an outer ring having an outer diametric surface provided with one or more annular groove, in which case the elastic member as the gap adjusting member comprises an O-ring engaged in the annular groove. If the elastic member is employed in the form of the O-ring, the elastic member can be easily provided on the outer periphery of the rolling member and the assemblability increases accordingly.

The elastic member as the gap adjusting unit may be what is coated on an outer peripheral surface of the rotary shaft support member. If the elastic member is coated on an outer peripheral surface of the rotary shaft support member, the elastic member can be easily provided on the outer periphery of the rotary shaft supporting member and the assemblability increases accordingly.

The gap dimension is preferred to be within the range of +100 μm to −10 μm. In general, if the gap dimension is too large, vibration of the rotary shaft becomes considerable. For this reason, it is preferred that the gap dimension is as small as possible. However, in the event that the spindle guide section used is of the curved shape, the assemblability will be adversely affected if a certain gap dimension is not available. Where the spindle guide section used is of the linear shape or a shape approximating to the linear shape, the gap can be rendered a negative gap. Although the use of the negative gap makes it possible to fix the rolling bearings firmly, the use of an extreme negative gap may result in reduction of the assemblability. From a series of experiments conducted, it has been ascertained that the gap dimension is preferably within the above described range.

In the present invention, it is recommended that at least one end of the guide pipe is fixed to the outer shell pipe or a member fixed to the outer shell pipe. In such case, the end of the guide pipe may be fixed by means of any one of screwing, press-fitting, bonding and welding. When at least one end of the guide pipe is fixed to the outer shell pipe or the member fixed to the outer shell pipe, the axial movement of the guide pipe is restrained and the guide pipe is made hard to move within the outer shell pipe. The use of any one of the screwing, press-fitting, bonding and welding is effective to facilitate a fixing of the end of the guide pipe.

In the present invention, the use may be made of a compressive force applying unit for applying an axially acting compressive force to the guide pipe. The provision of this compressive force applying unit is effective to allow the guide pipe to deform to such an extent as to diminish the gap between the guide pipe and the outer shell pipe to thereby restrain the guide pipe from moving within the outer shell pipe. Also, since the force is applied from the opposite ends of the guide pipe, the guide pipe is restrained from moving in the axial direction.

In the present invention, the spindle guide section may have a curved portion. Since the attitude altering member is flexible, it can be selectively advanced or retracted even though the spindle guide section has the curved portion.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

FIG. 2A is a sectional view showing a distal end member and the spindle guide section both employed in the remote controlled actuator according to the first embodiment of the present invention;

FIG. 2B is a cross sectional view taken along the line IIB-IIB in FIG. 2A;

FIG. 2C is a diagram showing a coupling structure through which the distal end member and a rotary shaft are connected with each other;

FIG. 4A is a sectional view showing the distal end member and the spindle guide section both employed in the remote controlled actuator according to a second preferred embodiment of the present invention;

FIG. 4B is a cross sectional view taken along the line IVB-IVB in FIG. 4A;

FIG. 8A is a sectional view showing the distal end member and the spindle guide section both employed in the remote controlled actuator according to a third preferred embodiment of the present invention;

FIG. 8B is a cross sectional view taken along the line VIIIB-VIIIB in FIG. 8A;

FIG. 8C is a cross sectional view taken along the line VIIIC-VIIIC in FIG. 8A;

FIG. 9A is a sectional view showing the distal end member and the spindle guide section both employed in the remote controlled actuator according to a fourth preferred embodiment of the present invention;

FIG. 9B is a cross sectional view taken along the line IXB-IXB in FIG. 9A;

FIG. 9C is a cross sectional view taken along the line IXC-IXC in FIG. 9A;

FIG. 11A is a sectional view showing the distal end member and the spindle guide section both employed in the remote controlled actuator according to a sixth preferred embodiment of the present invention;

FIG. 11B is a top plan view of the distal end member and the spindle guide section;

FIG. 11C is a cross sectional view taken along the line XIC-XIC in FIG. 11A;

FIG. 12A is a sectional view showing the distal end member and the spindle guide section both employed in the remote controlled actuator according to a seventh preferred embodiment of the present invention;

FIG. 12B is a top plan view of the distal end member and the spindle guide section;

FIG. 12C is a cross sectional view taken along the line XIIC-XIIC in FIG. 12A;

FIG. 13A is a sectional view showing the distal end member and the spindle guide section both employed in the remote controlled actuator according to an eighth preferred embodiment of the present invention;

FIG. 13B is a cross sectional view taken along the line XIIIB-XIIIB in FIG. 13A;

FIG. 14A is a sectional view showing the distal end member and the spindle guide section both employed in the remote controlled actuator according to a ninth preferred embodiment of the present invention;

FIG. 14B is a cross sectional view taken along the line XIVB-XIVB in FIG. 14A;

FIG. 16A is a sectional view showing the distal end member and the spindle guide section both employed in the remote controlled actuator according to a tenth preferred embodiment of the present invention;

FIG. 16B is a cross sectional view taken along the line XVIB-XVIB in FIG. 16A;

FIG. 17A is a sectional view showing the distal end member and the spindle guide section both employed in the remote controlled actuator according to an eleventh preferred embodiment of the present invention;

FIG. 17B is a cross sectional view taken along the line XVIIB-XVIIB in FIG. 17A;

FIG. 17C is a diagram showing a housing for the distal end member as viewed from a base end side;

FIG. 18A is a sectional view showing the distal end member and the spindle guide section both employed in the remote controlled actuator according to a twelfth preferred embodiment of the present invention;

FIG. 18B is a cross sectional view taken along the line XVIIIB-XVIIIB in FIG. 18A;

FIG. 18C is a diagram showing the coupling structure through which the distal end member and the rotary shaft are connected with each other.

DESCRIPTION OF PREFERRED EMBODIMENTS

Figure 1A:
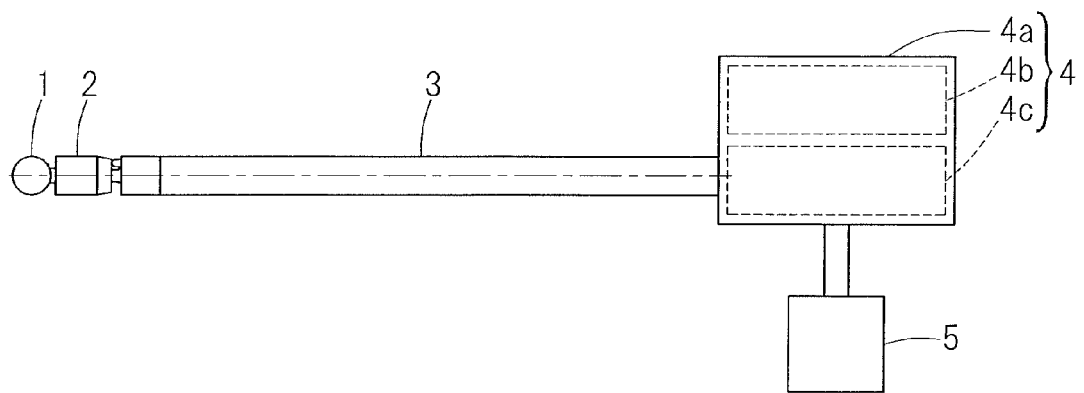
FIG. 1A is a diagram showing a schematic structure of a remote controlled actuator according to a first preferred embodiment of the present invention.
Figure 1B:
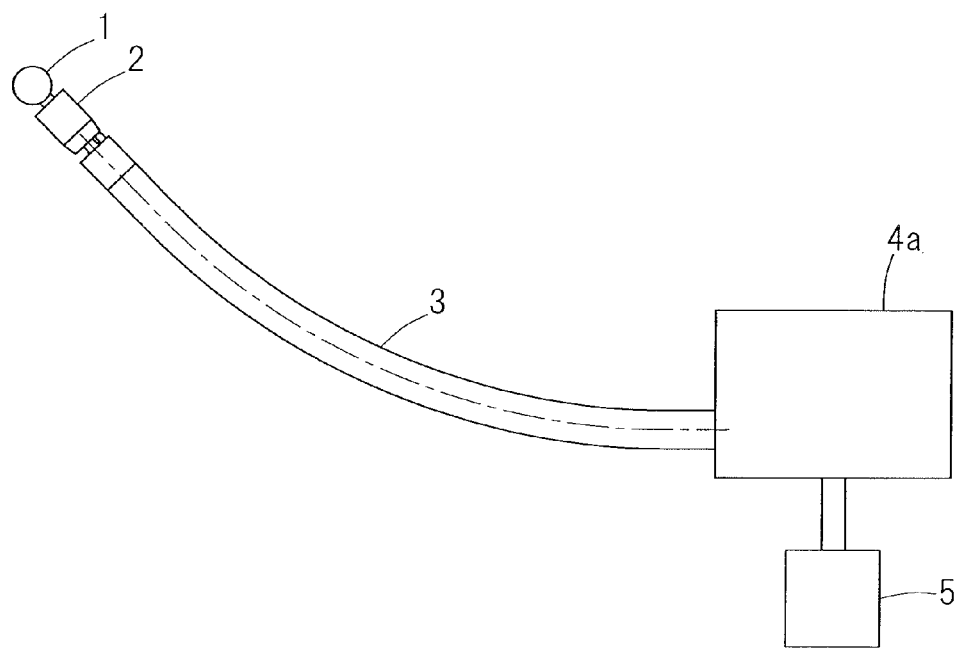
FIG. 1B is a diagram showing a schematic structure of the remote controlled actuator with a spindle guide section of a shape different from that shown in FIG. 1A.

A remote controlled actuator designed in accordance with a first preferred embodiment of the present invention will be described with particular reference to FIGS. 1A and 1B to FIGS. 3A and 3B. FIG. 1A illustrates the remote controlled actuator utilizing a spindle guide section 3 of a linear configuration and FIG. 1B illustrates the remote controlled actuator utilizing the spindle guide section 3 of a curved configuration. Referring particularly to FIG. 1A, the illustrated remote controlled actuator includes a distal end member 2 for holding a rotary tool 1, the elongated spindle guide section 3 having a distal end to which the distal end member 2 is fitted for alteration in attitude thereof, a drive unit housing 4a to which a proximal end of the spindle guide section 3 is connected, and a controller 5 for controlling a tool rotation drive mechanism 4b and an attitude altering drive mechanism 4c, both accommodated within the drive unit housing 4a. The drive unit housing 4a cooperates with the built-in tool rotation drive mechanism 4b and the similarly built-in attitude altering drive mechanism 4c to constitute a drive unit 4.

FIG. 2A illustrates a sectional representation of the distal end member 2 and the spindle guide section 3 both employed in the remote controlled actuator shown in FIG. 1A. The distal end member 2 includes a generally or substantially cylindrical housing 11 and a spindle 13 rotatably accommodated within such cylindrical housing 11 through a pair of bearings 12. The spindle 13 is of a tubular shape having a distal side opening and has a hollow defined therein, and a tool 1 is drivingly coupled with the spindle 13. Specifically, a shank portion 1a of the tool 1 is inserted into the hollow of the spindle 13 and is then coupled with such spindle 13 by means of a stop pin 14 for rotation together with the spindle 13. The distal end member 2 of the structure described above is coupled with a distal end of the spindle guide section 3 through a distal end member coupling unit 15. The distal end member coupling unit 15 supports the distal end member 2 for displacement in attitude and is comprised of a spherical bearing. More specifically, the distal end member coupling unit 15 includes a guided member 11a in the form of an inner diameter reduced portion at a base end of the housing 11, and a guide member 21a in the form of a collar integral with a constraint member 21 fixed to the tip of the spindle guide section 3. The guided member 11a and the guide member 21a have respective guide faces F1 and F2 that are held in sliding contact with each other, and those guide faces F1 and F2 have respective centers of curvature lying at a point O on the center line or longitudinal axis CL of the spindle 13, having their diameters being reduced towards the base end of the spindle 13. Accordingly, not only can the distal end member 2 be immovably constrained relative to the spindle guide section 3, but it can also be supported for displacement in attitude so that the attitude of the distal end member 2 can be altered.

The spindle guide section 3 includes a rotary shaft 22 for transmitting a rotational force exerted by a tool rotating drive source 41 (FIG. 3A) accommodated within the drive unit housing 4a. In the illustrated example, the rotary shaft 22 is employed in the form of a wire capable of undergoing deformation to a certain extent. Material for the wire includes, for example, metal, resin or glass fiber. The wire may be either a single wire or a stranded wire. As best shown in FIG. 2C, the spindle 13 and the rotary shaft 22 are coupled together by means of a universal joint 23 for transmitting rotation from the rotary shaft 22 to the spindle 13. The universal joint 23 is made up of a groove 13a, defined in a closed base end of the spindle 13, and of a projection 22a defined in a distal end of the rotary shaft 22 and engageable in the groove 13a. The center of joint between the groove 13a and the projection 22a is located at the same position as the centers of curvature O of the guide faces F1 and F2. It is, however, to be noted that the rotary shaft 22 and the projection 22a may be formed of members separate from each other.

The spindle guide section 3 has an outer shell pipe 25, which forms an outer shell for the spindle guide section 3, and the rotary shaft 22 is positioned at a center of this outer shell pipe 25. The rotary shaft 22 so positioned is rotatably supported by a plurality of rolling bearings 26, which form respective rotary shaft support member, positioned spaced a distant apart from each other in a direction axially of the spindle guide section 3. Between the neighboring rolling bearings 26, spring elements 27A for generating a preload on the inner rings 26a of the corresponding rolling bearing 26 and spring elements 27B for generating the preload on the outer rings 26b of the corresponding rolling bearings 26 are alternately disposed relative to each other. Those spring elements 27A and 27B may be employed in the form of, for example, compression springs. The constraint member 21 referred to previously is fixed to a pipe end portion 25a of the outer shell pipe 25 by means of a fixing pin 28 and has its distal end inner peripheral portion supporting a distal end of the rotary shaft 22 through a rolling bearing 29. It is, however, to be noted that the pipe end portion 25a may be a member separate from the outer shell pipe 25 and may then be connected with the outer shell pipe 25 by means of, for example, welding.

A hollow guide pipe 30 extending to opposite ends thereof is provided between an inner diametric surface of the outer shell pipe 25 and the rotary shaft 22. Within a guide hole 30a which is an inner diametric hole of this guide pipe 30, an attitude altering or operating member 31 is reciprocally movably inserted. In the instance as shown, the attitude altering member 31 is in the form of a wire 31a and pillar shaped pins 31b connected to a tip end of the wire 31a. The attitude altering member 31 has a tip end representing a spherical shape which is held in contact with a bottom face of a base end face 11b formed in a base (or proximal) end face of the housing 11, which defines a surface of contact between the distal end member 2 and the attitude altering member 31. The base end face 11b of the housing 11 is rendered to be an inclined face having its outer diametric side closer to the side of the spindle guide section 3. The other of the pillar shaped pins 31b that is closer to the drive unit housing 4a also has a tip end representing a spherical shape which is held in contact with a lateral surface of a pivot lever 43b (FIG. 3A) which will be explained in detail later. It is to be noted that except for the pillar shaped pins 31b, the attitude altering member 31 may be comprised of only the single wire 31a.

Between the base end face 11b of the housing 11 of the distal end member 2 and a tip end face of the outer shell pipe 25 of the spindle guide section 3, a restoring elastic member 32 made of, for example, a compression coil spring, is arranged at a location spaced 180° degrees circumferentially in phase from the circumferential location where the attitude altering member 31 is positioned. The restoring elastic member 32 biases the distal end member 2 towards a predetermined attitude.

Also, as best shown in FIG. 2A, a plurality of reinforcement shafts 34, separate from the guide pipe 30, are arranged between the inner diametric surface of the outer shell pipe 25 and the rotary shaft 22 on the same pitch circle C1 as that depicted by the guide pipe 30. Those reinforcement shafts 34 are employed for securing the rigidity of the spindle guide section 3. Each of the reinforcement shafts 34 has an outer diameter which is equal to that of the guide pipe 30. The guide pipe 30 and the plural reinforcement shafts 34 are spaced an equal distance from each other.

Assuming that the inner diametric dimension of the outer shell pipe 25 is expressed by D1, the outer diametric dimension of each of the guide pipe 30 and the reinforcement shafts 34 is expressed by D2 and the outer diametric dimension of each of the rolling bearings 26 is expressed by D3, those dimensions are so selected as to establish such a relationship of $D1 \leq D2 \times 2 + D3$. In other words, a space between the outer shell pipe 25 and any one of the guide pipe 30 and each reinforcement shaft 34 is rendered to be no gap or a negative gap and, similarly, a space between any one of the guide pipe 30 and each reinforcement shaft 34 and each of the rolling bearings 26 is rendered to be no gap or a negative gap.

Accordingly, the guide pipe 30 and the reinforcement shafts 34 are urged against the inner diametric surface of the outer shell pipe 25 and also against an outer diametric surface of each of the rolling bearings 26. For this reason, the guide pipe 30 and the reinforcement shafts 34 are restrained from moving within the outer shell pipe 25 in a direction radially of the outer shell pipe 25. Also, even the presence of a friction taking place in respective contact surfaces between both of the guide pipe 30 and the reinforcement shafts 34 and both of the outer shell pipe 25 and the rolling bearings 26 makes it difficult for both of the guide pipe 30 and the reinforcement shaft 34 to move. In other words, in the instance now under discussion, the outer shell pipe 25 and the rolling bearings 26 form respective guide pipe restraining units 50 for restraining the guide pipe 30 from moving within the outer shell pipe 25.

More specifically, by adjusting at least one or more of the inner diametric dimension D1 of the outer shell pipe 25, the outer diametric dimension D2 of each of the guide pipe 30 and the reinforcement shafts 34 and the outer diametric dimension D3 of each of the rolling bearings 26, the previously described relationship can establish. By way of example, while a plurality of guide pipes 30 and reinforcement shafts 34 having respective diametric dimensions D2 that are different from each other are prepared for, some of them that are suitable are selectively used. Similarly, a plurality of rolling bearings 26 having the different outer diametric dimensions D3 may be prepared for the selection, and/or a plurality of outer shell pipes 25 having different inner diametric dimensions D1 may be prepared for the selection. According to this method, the spindle guide section 3 can be manufactured at a reduced cost because high dimensional accuracies of those component parts 25, 26, 30 and 34 are not called for.

In the case where the remote controlled actuator makes use of the spindle guide section 3 of a curved configuration as shown in FIG. 1B, although not shown, it is necessary that the outer shell pipe 25, the guide pipe 30 and the reinforcement shafts 34 must be correspondingly curved. It is recommended to use an easily deformable material for the rotary shaft 22 and, for example, a shape memory alloy is a suitable material for the rotary shaft 22. Other structural features than those described above are similar to those in the linear spindle guide section 3 described previously.

Figure 3A:
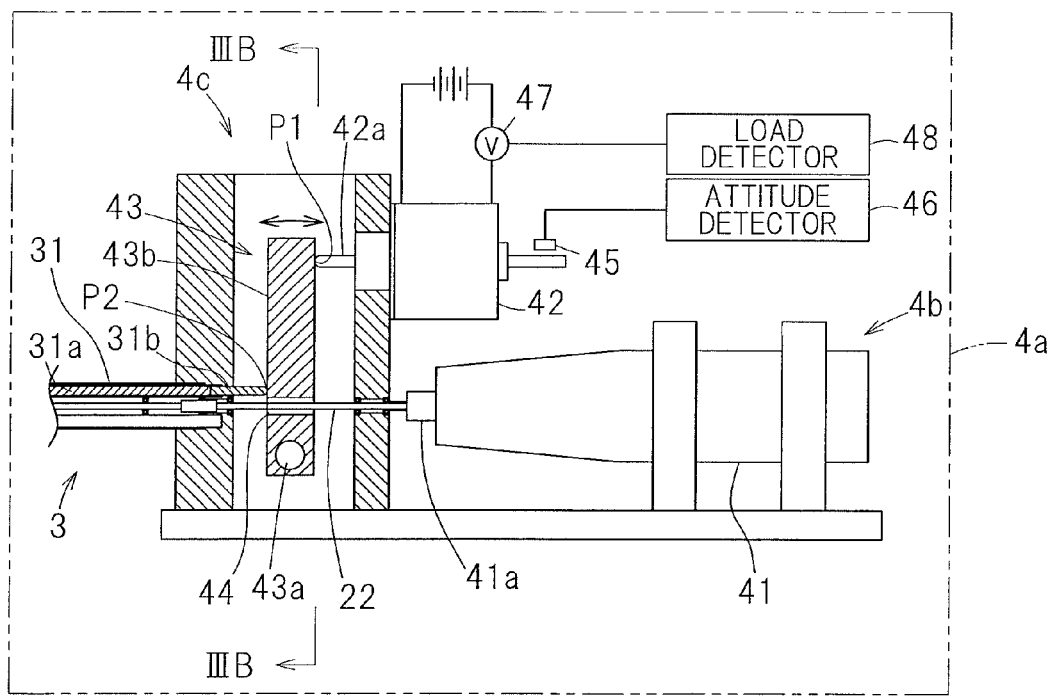
FIG. 3A is a sectional view showing a tool rotation drive mechanism and an attitude altering drive mechanism both employed in the remote controlled actuator.
Figure 3B:
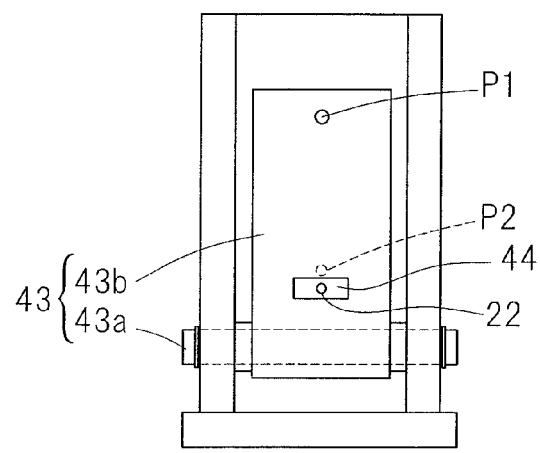
FIG. 3B is a cross sectional view taken along the line IIIB-IIIB in FIG. 3A.

The tool rotating drive mechanism 4b and the attitude altering drive mechanism 4c, both housed within the drive unit housing 4a, are best shown in FIG. 3A. The tool rotating drive mechanism 4b makes use of a tool rotating drive source 41. This tool rotating drive source 41 is in the form of, for example, an electric motor, having its output shaft 41a coupled with a base end or proximal end of the rotary shaft 22. The rotary shaft 22 extends through an opening 44 defined in the pivot lever 43b which will be explained in detail later.

The attitude altering drive mechanism 4c makes use of an attitude altering drive source 42 that is associated, with the attitude altering member 31. The attitude altering drive source 42 may be in the form of, for example, electrically operated linear actuator having an output rod 42a, the movement of the output rod 42a in one of leftward and rightward directions on the drawing plane of FIG. 3A one at a time being transmitted to the corresponding attitude altering member 31 through a force increasing and transmitting mechanism 43. The force increasing and transmitting mechanism 43 includes a pivot lever 43b pivotable about a support pin 43a and is so designed and so configured as to allow a force of the output rods 42a to work on a working point P1 of the lever 43b, which are respectively spaced a long distance from the support pin 43a, and as to apply a force to the attitude altering member 31 at a force point P2, which are spaced a short distance from the support pin 43a, wherefore the output of the attitude altering drive sources 42 can be increased and then transmitted to the attitude altering member 31. Since the use of the force increasing and transmitting mechanism 43 is effective to enable a large force to be applied to the attitude altering members 31 even in the linear actuator of a low output capability, the linear actuator can be downsized. The attitude altering drive source 42 may be a rotary motor. Alternatively, instead of the use of linear actuators or the like, the attitude of the distal end member 2 may be manually operated from a remote site by remote control.

The attitude altering drive mechanism 4c is provided with an operating amount detector 45 for detecting the operating amount of the attitude altering drive source 42. The detection value outputted from this operating amount detector 45 is outputted to an attitude detector 46. The attitude detector 46 is operable to detect the attitude inclined about the X-axis and Y-axis (FIG. 2B) of the distal end member 2. The attitude detector 46 includes a relation setting unit (not shown), in which the relation between the output signal of the operating amount detector 45 and the attitude of the distal end member 2 inclined is set in terms of an arithmetic equation or table, and makes use of the relation setting means to detect the inclination in attitude in reference to the output signal inputted. This attitude detector 46 may be provided either in the controller 5 (FIG. 1A) or in an external control device.

Also, the attitude altering drive mechanism 4c is provided with a supply power meter 47 for detecting the electric energy supplied to the attitude altering drive source 42, which is an electrically operated actuator. The detection value of this supply power meter 47 is outputted to a load detector 48. This load detector 48 in turn detects a load acting on the distal end member 2 in reference to the output of the supply power meter 47. This load detector 48 includes a relation setting unit (not shown), in which the relation between the load and the output signal of the supply power meter 47 is set in terms of an arithmetic equation or table, and makes use of the relation setting unit to detect the load in reference to the output signal so inputted. This load detector 48 may be provided either in the controller 5 (FIG. 1A) or in an external control device.

The controller 5 referred to above is operable to control the tool rotation drive sources 41 and the attitude altering drive source 42, based on the respective detection values outputted by the attitude detector 46 and the load detector 48.

The operation of the remote controlled actuator of the construction hereinabove described will now be described in detail.

When the tool rotating drive source 41 as shown in FIG. 3A is driven, the rotational force thereof is transmitted to the spindle 13 shown in FIG. 2A through the rotary shaft 22 to thereby rotate the tool 1 together with the spindle 13. The load acting on the distal end member 2 when the tool 1 then being rotated cuts a bone or the like is detected from the detection value of the supply power meter 47 shown in FIG. 3A by the load detector 48. Accordingly, when the amount of feed of the remote controlled actuator in its entirety and the alteration of attitude of the distal end member 2, as will be described later, are controlled in dependence on the value of the load detected in the manner described above, cutting of the bone can be properly carried out while the load acting on the distal end member 2 is maintained properly.

When in use, the attitude altering drive source 42 is driven to cause the distal end member 2 to alter in attitude by remote control. By way of example, if the attitude altering member 31 shown in FIG. 2A is advanced by the attitude altering drive source 42 in a direction towards the tip or distal side, the housing 11 for the distal end member 2 is pressed by the attitude altering member 31 with the distal end member 2 consequently altered in attitude along the guide faces F1 and F2 so that the tip or distal side can be oriented downwardly as viewed in FIG. 2A. If the attitude altering member 31 is conversely retracted by the attitude altering drive source 42, the housing 11 for the distal end member 2 is pressed backwardly by the effect of the elastic repulsive force exerted by the restoring elastic member 32 and, consequently, the distal end member 2 is altered in attitude along the guide faces F1 and F2 so that the tip or distal side can be oriented upwardly as viewed in FIG. 2A. At this time, a pressure from the attitude altering member 31, the elastic repulsive force from the restoring elastic member 32 and a reactive force from the constraint member 21 are applied to the distal end member coupling unit 15 and, depending on the balance of those applied forces, the attitude of the distal end member 2 is determined. The attitude of the distal end member 2 is detected by the attitude detector 46 from the detection value of the operating amount detector 45 (FIG. 3A). For this reason, the attitude of the distal end member 2 can be properly controlled by remote control.

Since the base end face 11b of the housing 11 of the distal end member 2 is rendered to be an inclined face having its outer diametric side closer to the side of the spindle guide section 3, the base end face 11b of the housing 11 can be easily slid relative to the attitude altering members 31 when the attitude altering members 31 are pressing the base end face 11b of the housing 11, resulting in a smooth attitude alteration of the housing 11.

Since the attitude altering member 31 is inserted through the guide hole 30a of the guide pipe 30, the attitude altering member 31 can properly act on the distal end member 2 at all times without being accompanied by displacement in position in a direction perpendicular to the lengthwise direction thereof and the attitude altering operation of the distal end member 2 can therefore be performed accurately. Also, since the attitude altering member 31 is made up of a wire and has a flexible property, the attitude altering operation of the distal end member 2 is carried out accurately even when the spindle guide section 3 is curved. In addition, since the center of the junction between the spindle 13 and the rotary shaft 22 lies at the same position as the respective centers of curvature O of the guide faces F1 and F2, no force tending to press and pull will not act on the rotary shaft 22 as a result of the alteration of the attitude of the distal end member 2 and the distal end member 2 can be smoothly altered in attitude.

Since the guide pipe restraining unit 50 for restraining the guide pipe 30 from moving within the outer shell pipe 25 is employed, the rigidity of the guide pipe 30 can be maintained high. Accordingly, a displacement or force of the attitude altering drive source 42 provided in the drive unit housing 4a can be accurately transmitted to the distal end member 2 and therefore the positioning accuracy of the tool 1 is enhanced In the event that the guide pipe 30 moves within the outer shell pipe 25, the displacement or force of the attitude altering drive source 42 gets away in a direction radially of the guide pipe 30 at the time such displacement or force is transmitted to the distal end member 2 through the attitude altering member 31 within the guide pipe 30, and, therefore, the displacement or force of the attitude altering drive source 42 will not be accurately transmitted to the distal end member 2, resulting in worsening of the positioning accuracy of the tool 1.

Since the rotary shaft 22 is rotatably supported by the rolling bearings 26, which are rotary shaft support members, it is possible to transmit the rotation of the tool rotation drive source 41 to the spindle 13 by driving the rotary shaft 22 at a high speed. Since the rolling bearings 26 are preloaded by means of the spring elements 27A and 27B, the support rigidity of the rolling bearings 26 is so high as to permit the rotary shaft 22 to be driven at a high speed. Since the spring elements 27A and 27B are positioned each between the neighboring rolling bearings 26, the spring elements 27A and 27B can be provided without increasing the diameter of the spindle guide section 3. In this way, since the rotary shaft 22 can be driven at a high speed, the processing can be performed with the tool 1 driven at the high speed. For this reason, a surface to be cut can be finished beautifully and the cutting resistance acting on the tool 1 can be reduced.

It is necessary to provide the rotary shaft 22 and the attitude altering member 31 within the spindle guide section 3 of the elongated configuration in a protected fashion. In this respect, as shown in FIG. 2B, the rotary shaft 22 is provided at the center of the outer shell pipe 25, and the guide pipe 30, accommodating therein the attitude altering member 31, and the reinforcement shafts 34 are arranged between the outer shell pipe 25 and the rotary shaft 22 in a direction circumferentially of the spindle guide section 3. Therefore, the rotary shaft 22 and the attitude altering member 31 can be protected and the interior of the spindle guide section 3 can be made hollow to thereby reduce the weight and also to secure the rigidity. Also, a good balance as a whole is preserved.

The remote controlled actuator of the foregoing construction is utilized in grinding the femoral marrow cavity during, for example, the artificial joint replacement surgery and during the surgery, it is used with the distal end member 2, shown in FIG. 2A, in its entirety or a part thereof inserted into the body of a patient. Because of this, with such distal end member 2 as described above that can be altered in attitude by remote control, the bone can be processed in a condition with the tool 1 maintained in a proper attitude at all times and the opening for insertion of the artificial joint can be finished accurately and precisely. With the spindle guide section 3 of the curved shape, the distal end member 2 may be inserted into a deeper area than that afforded by the spindle section 3 of the linear shape. Accordingly, when one of the spindle guide sections 3 of the linear and curved shapes as shown in FIGS. 1A and 1B, respectively, are selectively employed, the portal or the bore for the insertion of the artificial joint can be accurately finished during the artificial joint replacement surgery.

Figure 5:
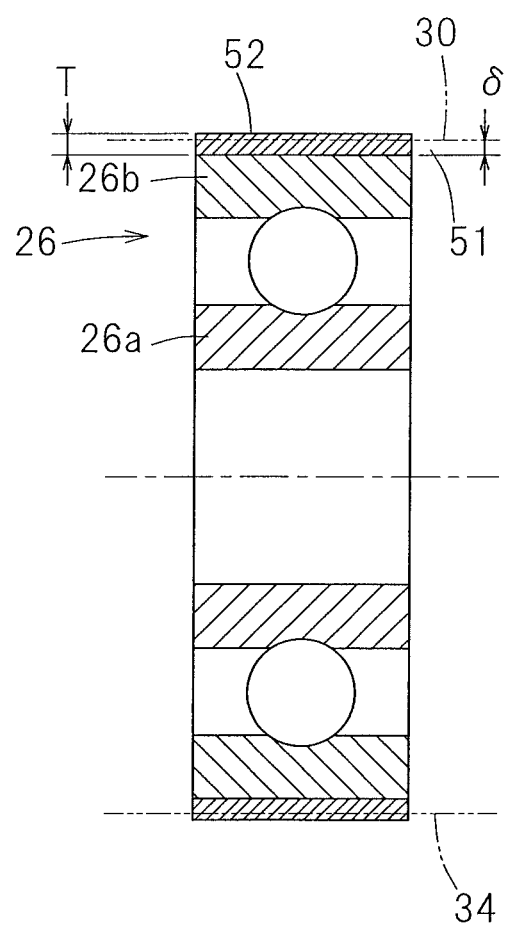
FIG. 5 is a sectional view showing a rotary shaft support member and a guide pipe suppressing unit both employed in the remote controlled actuator.

A second preferred embodiment will now be described in detail with particular reference to FIGS. 4A and 4B and FIG. 5. The guide pipe restraining unit, now identified by 50A, employed in the practice of this second embodiment is of a structure different from that of the guide pipe restraining unit 50 employed in the practice of the previously described first embodiment. Specifically, as best shown in FIG. 5, a gap 51 exists between each of the rolling bearings 26 and any one of the guide pipe 30 and the reinforcement shafts 34, and an annular elastic member 52 is provided on the outer diametric surface of an outer ring 26b of each rolling bearing 26 so as to fill up the gap 51. This elastic member 52 is of a strip-like shape having a width equal to the axial length of the outer ring 26b and covers the entire axial area of the outer diametric surface of the outer ring 26b. Material for the elastic member 52 is preferably of a kind having a low hardness, for example, a rubber material such as silicone rubber, or a resinous material such as a fluorine resin.

In such case, as shown in FIG. 4B, the relationship among the inner diametric dimension D1 of the outer shell pipe 25, the outer diametric dimension D2 of the guide pipe 30 and each reinforcement shaft 34 as a member of the same outer diameter, which is a member of the same outer diameter, as the guide pipe 30, and the outer diametric dimension D3 of each rolling bearing 26 is so chosen as to satisfy $D1 \geq D2 \times 2 + D3$. In other words, a space between the outer shell pipe 25 and any one of the guide pipe 30 and each reinforcement shaft 34 is rendered to be no gap or a positive gap and, similarly, a space between any one of the guide pipe 30 and each reinforcement shaft 34 and each of the rolling bearings 26 is rendered to be no gap or a positive gap. However, the thickness T of the elastic member 52, when in a condition with no external force applied, is chosen to be greater than the gap dimension 6.

The provision of the elastic members 52 in the manner described above is effective to allow the guide pipe 30 and the reinforcement shafts 34 to be urged towards the inner diametric surface of the outer shell pipe 25 by an elastic deformation thereof. For this reason, the guide pipe 30 and the reinforcement shafts 34 are restrained from moving within the outer shell pipe 25 in a direction radially of the outer shell pipe 25. Also, even in the presence of the friction between the surfaces of contact of the guide pipe 30 and the reinforcement shafts 34 with the outer shell pipe 25, the guide pipe 30 and the reinforcement shafts 34 are rendered difficult to move. In other words, in the embodiment now under discussion, the outer shell pipe 25, the rolling bearings 26 and the elastic members 52 altogether constitute the guide pipe restraining unit 50A for restraining the guide pipe 30 from moving within the outer shell pipe 25.

Figure 6:
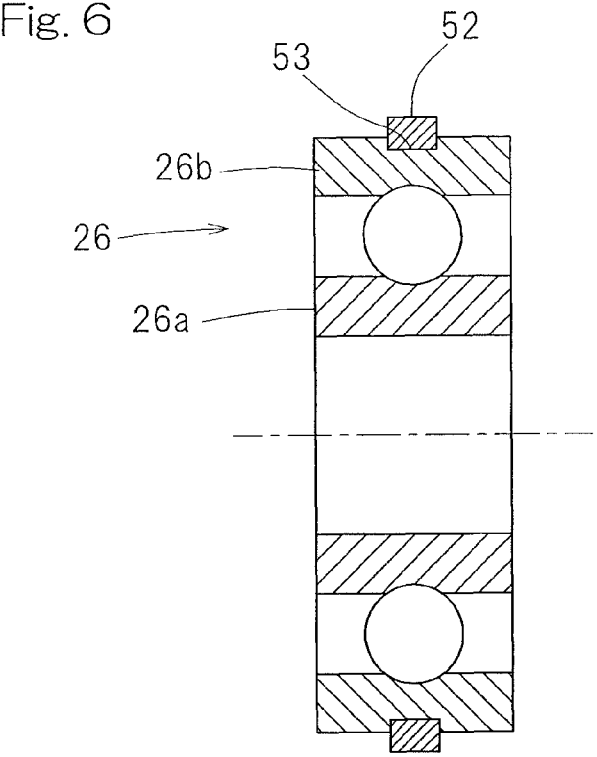
FIG. 6 is a sectional view showing the rotary shaft support member and the guide pipe suppressing unit both employed in a first modified example.

FIG. 6 illustrates a first modified example of each of the elastic member as the guide pipe restraining unit. The elastic member 52 according to this first modified example is of a narrow strip-like shape and is mounted inside an annular groove 53 defined in the outer diametric surface of the outer ring 26b of the respective rolling bearing 26. Positioning the elastic member 52 within the annular groove 53 is effective to avoid an undesirable separation of the elastic member 52 from the outer diametric surface of the outer ring 26b.

Figure 7:
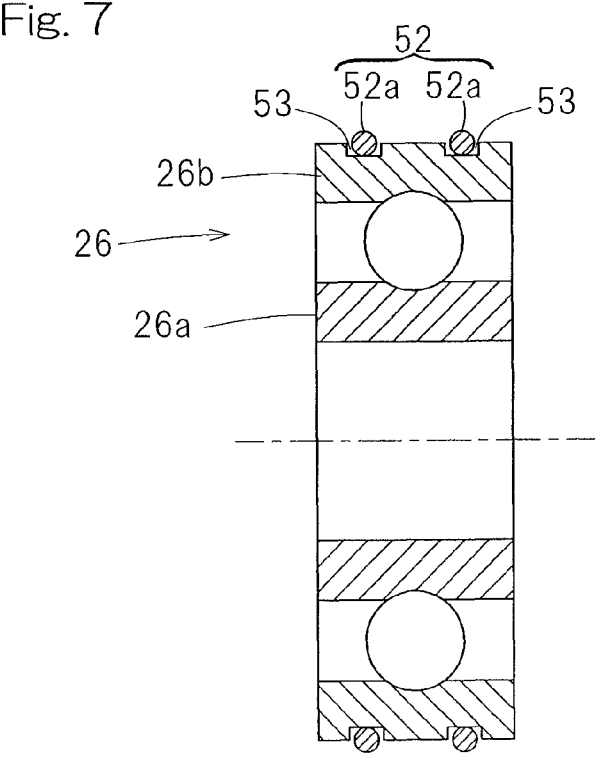
FIG. 7 is a sectional view showing the rotary shaft support member and the guide pipe suppressing unit both employed in a second modified example.

FIG. 7 illustrates a second modified example of each of the elastic member. The elastic member 52 according to this second modified example is made up of two O-rings 52a that are mounted inside respective annular grooves 53 defined in the outer diametric surface of the outer ring 26b of each of the rolling bearings 26. The use of the elastic member 52 in the form of the O-rings 52a is effective to allow the elastic member 52 to be easily mounted on the outer diametric surface of the outer ring 26b, resulting in a good assemblability. In this second modified example, since each elastic member 52 is comprised of the two O-rings 52a, the respective rolling bearings 26 can be stably fixed and, even when the moment load acts on the rolling bearing 26, the two point support is effective to reduce the moment load or the like acting on the rolling bearings 26 through deformation of the O-rings 52a without the support rigidity being reduced extremely.

A third preferred embodiment of the present invention will be hereinafter described in detail with particular reference to FIGS. 8A to 8C. The guide pipe restraining unit, now identified by 50B, employed in the practice of this third embodiment is of a structure different from the guide pipe restraining unit 50 employed in the practice of the previously described first embodiment of the present invention. In other words, as best shown in FIG. 8A, the guide pipe restraining unit 50B makes use of a guide pipe contact member 55 disposed between the neighboring rolling bearings 26 for contacting the guide pipe 30 and the reinforcement shafts 34. This guide pipe contact member 55 is of a shape sufficient to contact respective surfaces of the guide pipe 30 and the reinforcement shafts 34, which are respectively situated on inner diametric sides thereof with respect to the outer shell pipe 25. The guide pipe contact member 55 is provided at an axial location where the inner ring spring element 27A is disposed, and the inner diameter of this guide pipe contact member 55 is chosen to be greater than the outer diameter of the inner ring spring element 27A. Accordingly, interference between the spring elements 27A, 27B and the guide pipe contact member 55 can be avoided. As FIG. 8B makes it clear, the guide pipe 30 and the reinforcement shafts 34 are employed in one and five in number as is the case with those employed in the practice of the previously described first embodiment of the present invention.

Referring to FIG. 8C, by properly selecting the inner diametric dimension D1 of the outer shell pipe 25, the outer diametric dimension D2 of any one of the guide pipe 30 and the reinforcement shafts 34 and the shape and various dimensions of the guide pipe contact member 55, the guide pipe 30 and the reinforcement shafts 34 can be urged against the inner diametric surface of the outer shell pipe 25. For example, assuming that the diameter of the imaginary circle C2 connecting respective bottoms of recessed 55a, defined in the guide pipe contact member 55 for receiving therein the guide pipe 30 and the reinforcement shafts 34, is expressed by D4, such a relationship expressed by $D1 \leq D2 \times 2 + D4$ is chosen. In other words, a space between the outer shell pipe 25 and any one of the guide pipe 30 and each reinforcement shaft 34 is rendered to be no gap or a negative gap and, similarly, a space between any one of the guide pipe 30 and each reinforcement shaft 34 and each of the guide pipe contact member 55 is rendered to be no gap or a negative gap. By so doing, the gap between the guide pipe 30 and the outer shell pipe 25 is eliminated and, hence, the guide pipe 30 is rendered difficult to move within the outer shell pipe 25. Also, due to the friction taking place between the respective surfaces of contact of the guide pipe 30 and the outer shell pipe 25, the guide pipe 30 is rendered difficult to move.

A fourth preferred embodiment of the present invention will be described in detail with particular reference to FIGS. 9A to 9C. The guide pipe restraining unit, now identified by 50C, employed in the practice of this fourth embodiment is of a structure different from that of the guide pipe restraining unit 50 employed in the practice of the previously described first embodiment. In other words, as shown in FIG. 9A, the guide pipe restraining unit 50C makes use of a guide pipe contact member 55 that contacts the guide pipe 30 and the reinforcement shafts 34. The guide pipe contact member 55 has an outer diametric end extended to a position where it is brought into contact with the inner diametric surface of the outer shell pipe 25, as best shown in FIG. 9C, with the outer diametric end subsequently welded to the outer shell pipe 25 at weld deposits 56.

It is, however, to be noted that other than the welding used to fix the guide pipe contact member 55 to the inner diametric surface of the outer shell pipe 25 at the weld deposits 56, any other suitable method may be employed such as, for example, soldering.

With the guide pipe contact member 55 fixed to the outer shell pipe 25 in the manner described above, it is preferred that the guide pipe 30 is urged against the outer shell pipe 25. By so doing, a function and effects similar to those afforded by the previously described embodiment can be obtained. It is, however, to be noted that even though the guide pipe 30 is not urged against the outer shell pipe 25, a gap, within which the guide pipe 30 can move, can be minimized in the presence of the guide pipe contact member 55, and therefore, it is effective as the guide pipe restraining unit 50C. As FIG. 9B makes it clear, the guide pipe 30 and the reinforcement shafts 34 are employed respectively in one and five in number as are the case with those in the previously described first embodiment.

Figure 10A:
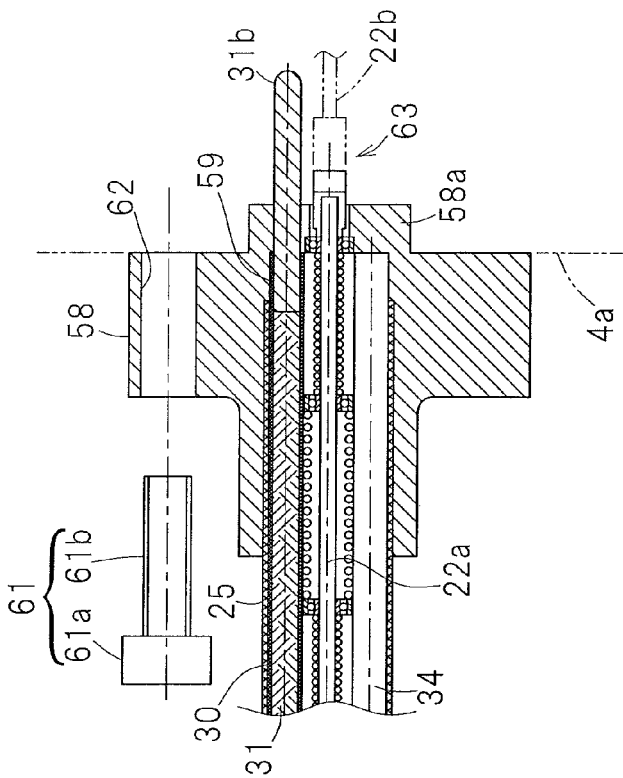
FIG. 10A is a sectional view showing the distal end member and the spindle guide section both employed in the remote controlled actuator according to a fifth preferred embodiment of the present invention.
Figure 10B:
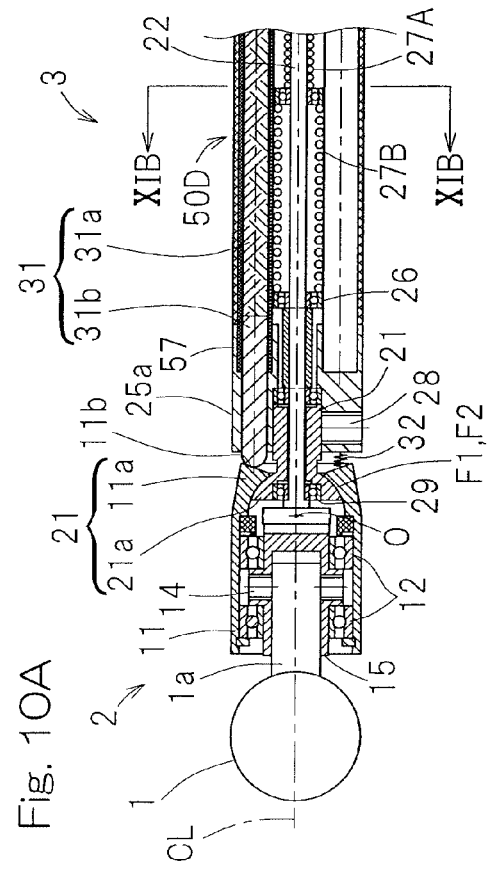
FIG. 10B is a cross sectional view taken along the line XIB-XIB in FIG. 10A.

A fifth preferred embodiment of the present invention will be hereinafter described in detail with particular reference to FIGS. 10A and 10B. The guide pipe restraining unit, now identified by 50D, employed in the practice of this fifth embodiment is of a structure different from that of the guide pipe restraining unit 50 employed in the practice of the previously described first embodiment. In other words, as best shown in FIG. 10A, the guide pipe restraining unit 50D is of a design in which at least one end of the guide pipe 30 is fixed to the outer shell pipe 25 or a member fixed to the outer shell pipe 25 so that the axial movement of the guide pipe 30 can be restrained, making the guide pipe 30 difficult to move within the outer shell pipe 25. In this embodiment, the distal end of the guide pipe 30 fixedly press-fitted into a hole 57 defined in the pipe end portion 25a of the outer shell pipe 25. Also, the base end portion of the guide pipe 30 is fixedly press-fitted in a groove 59 defined in a flange member 58, which is a member fixed to the outer shell pipe 25. The reinforcement shafts 34 have their opposite ends fixedly press-fitted into the hole 57 in the pipe end portion 25 and the groove 59 in the flange member 58, respectively. It is, however, to be noted that instead of the press-fitting, the opposite ends of the guide pipe 30 and the reinforcement shafts 34 may be fixedly threaded into, bonded to or welded to the hole 57 and the groove 59, respectively.

When the opposite ends of the guide pipe 30 are fixed as is the case with the fifth embodiment, an axially acting compressive force is applied to the guide pipe 30. In other words, the hole 57 in the pipe end portion 25a and the groove 59 in the flange member 58 form respective part of a compressive force applying unit for applying the axially acting compressive force to the guide pipe 30. The provision of this compressive force applying unit is effective to allow the guide pipe 30 to deform to such an extent as to diminish the gap between the guide pipe 30 and the outer shell pipe 25 to thereby restrain the guide pipe 30 from moving within the outer shell pipe 25. Also, since the force is applied from the opposite ends of the guide pipe 30, the guide pipe 30 is restrained from moving in the axial direction. It is, however, to be noted that even though only one end, not opposite ends, of the guide pipe 30 is fixed, a function of rendering the guide pipe 30 difficult to move within the outer shell pipe 25 can be obtained. The guide pipe restraining unit 50D of the type referred to above may be employed alone or in combination with any one of the guide pipe restraining units 50 to 50C which have been previously described. In this embodiment, as shown in FIG. 10B, a wide strip-like elastic member 52 is provided on the outer diametric surface of each of the rolling bearings 26 as one of the guide pipe restraining units 50 to 50C.

It is to be noted that in the remote controlled actuator employed in the embodiment shown in the fifth embodiment, the flange member 58 is connected with the drive unit housing 4a by means of a plurality of bolts 61 as shown in FIG. 10A and the spindle guide section 3 is detachable to the drive unit housing 4a. More specifically, the flange member 58 has a cylindrical protrusion 58a at a center portion of a base end face thereof and the connection is made with the cylindrical protrusion 58a inserted into a recess (not shown) defined in the drive unit housing 4a. The plural bolts 61 are arranged having been distributed in a direction circumferentially of the flange member 58, each having a bolt head 61a held in abutment with a side face of the flange member 58 remote from the drive unit housing 4a while a respective bolt shank 61b is threaded into a corresponding bolt hole (not shown), defined in the drive unit housing 4a, through an associated bolt insertion hole 62 in the flange member 58. The rotary shaft 22 employed in the practice of this fifth embodiment is made up of an in-section shaft portion 22a, positioned within the spindle guide section 3, and an in-house shaft portion 22b positioned within the drive unit housing 4a, and the in-guide shaft portion 22a and the in-housing shaft portion 22b are connected with each other through a coupling 63 so that those shaft portions 22a and 22b can be separated in a direction axially thereof and can be rotated together about the longitudinal axis of the rotary shaft 22.

Sixth and seventh preferred embodiments of the present invention are shown respectively in FIGS. 11A to 11C and 12A to 12C. The guide pipe restraining unit shown by 50E in FIGS. 11A and 11B in accordance with the sixth embodiment of the present invention is of a structure in which the peripheral wall of the outer shell pipe 25 has a window 71 defined therein so as to extend completely across the thickness of the peripheral wall thereof and a portion of the outer shell pipe 25 around the window 71 and the guide pipe 30 are fixed together by means of a solder deposit 72. As FIG. 11C makes it clear, the guide pipe 30 and the reinforcement shafts 34 are employed in one and five in number as is the case with those employed in the practice of the previously described first embodiment.

The guide pipe restraining unit shown by 50F in FIGS. 12A and 12B in accordance with the seventh embodiment of the present invention is of a structure in which, without the window 71 defined in the peripheral wall of the outer shell pipe 25 as shown in FIG. 11A, the outer shell pipe 25 and the guide pipe 30 are fixed together by means of a laser welding applied as at 73 from the side of the outer diametric surface of the outer shell pipe 25. It is to be noted that in those sixth and seventh embodiments, the attitude altering member 31 in its entirety is comprised of a wire. As FIG. 12C makes it clear, the guide pipe 30 and the reinforcement shafts 34 are employed in one and five in number as is the case with those employed in the practice of the previously described first embodiment.

As hereinabove described, with the guide pipe 30 fixed to the outer shell pipe 25 by means of the solder deposit 72 as in the sixth embodiment or the weld deposit 73 as in the seventh embodiment, the guide pipe 30 can be rendered immovable within the outer shell pipe 25. Also, in view of the fact that the outer shell pipe 25 and the guide pipe 30 are fixed together, the spindle guide section 3 has a section modulus increased to result in an increase of the rigidity. For this reason, even when a force acts on the distal end member 2, the spindle guide section 3 becomes hard to flex and, hence, the positioning accuracy of the distal end member 2 relative to the drive housing 4a increases.

The guide pipe restraining unit 50D or 50F designed in accordance with the sixth or seventh embodiments, respectively, may be employed alone or in combination with any one of the guide pipe restraining units 50 to 50D which have been previously described.

Reference will now be made to FIGS. 13A and 13B for the discussion of an eighth preferred embodiment of the present invention. As shown in FIG. 13B, the remote controlled actuator according to this fourth embodiment includes two guide pipes 30 spaced 180 degrees in phase relative to each other within an outer shell pipe 25 and each of the guide pipes 30 has an inner diametric hole functioning as a guide hole 30a within which an attitude altering member 31 is inserted for advancement and retraction. Between those two guide pipes 30, a plurality of reinforcement shafts 34 are arranged on the same pitch circle diameter C as that of the guide pipes 30. No restoring elastic member 32 is provided. The guide faces F1 and F2, shown in FIG. 13A, are spherical surfaces each having the center of curvature lying at the point O or cylindrical surfaces each having a lateral X-axis as a longitudinal axis passing through the point O.

The drive unit 4 (not shown) is provided with two attitude altering drive sources 42 (not shown) for selectively advancing and retracting respective attitude altering members 31 so that when those two attitude altering drive sources 42 are driven in respective directions opposite to each other, the distal end member 2 can be altered in attitude. By way of example, when the upper attitude altering member 31 shown in FIG. 13A is advanced towards the tip end side and the lower attitude altering member 31 is retracted, the housing 11 for the distal end member 2 is pressed by the upper attitude altering member 31 and, therefore, the distal end member 2 is altered in attitude along the guide surfaces F1 and F2 with the tip end side oriented downwards. Conversely, when both of the attitude altering members 31 are driven in the directions opposite thereto, the lower attitude altering member 31 urges the housing 11 for the distal end member 2 to allow the distal end member 2 to alter in attitude along the guide surfaces F1 and F2 with the distal end side oriented upwardly as viewed in FIG. 13A. At this time, the pressures from the upper and lower attitude altering members 31 and a reactive force from the constraint member 21 act on the distal end member connecting unit 15 and, accordingly, the attitude of the distal end member 2 is determined in dependence on the balance of those working forces. According to this construction, since the housing 11 for the distal end member 2 is pressed by the two attitude altering members 31, as compared with the previously described embodiment in which it is pressed by a single attitude altering member 31, the attitude stability of the distal end member 2 can be increased.

A ninth preferred embodiment of the present invention is shown in FIGS. 14A and 14B and FIGS. 15A and 15B, reference to which will now be made for the details thereof. As shown in FIG. 14B, in a remote controlled actuator of this embodiment three guide pipes 30 are provided within this outer shell pipe 25 at respective circumferential locations spaced 120° in phase from each other and the attitude altering members 31 (31U, 31L, 31R) are inserted within the guide hole 30a, each of which is an inner diametric hole of each of the guide pipes 30, for advancement and retraction. Between those three guide pipes 30, a plurality of reinforcement shafts 34 are arranged on the same pitch circle diameter C as that of the guide pipes 30 in an alternate manner. Each of the guide faces F1 and F2 shown in FIG. 14A is a spherical wall having its center of curvature lying at a point O and the distal end member 2 can be tiltable in any arbitrarily chosen direction.

Figure 15A:
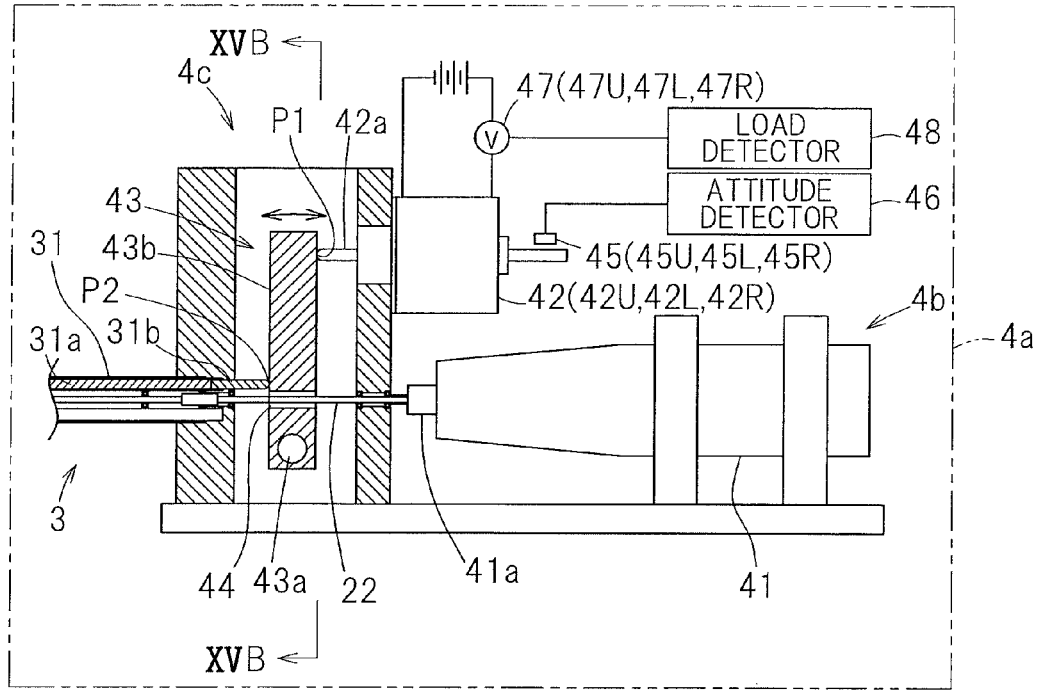
FIG. 15A is a sectional view showing the tool rotation drive mechanism and the attitude altering drive mechanism both employed in the remote controlled actuator.
Figure 15B:
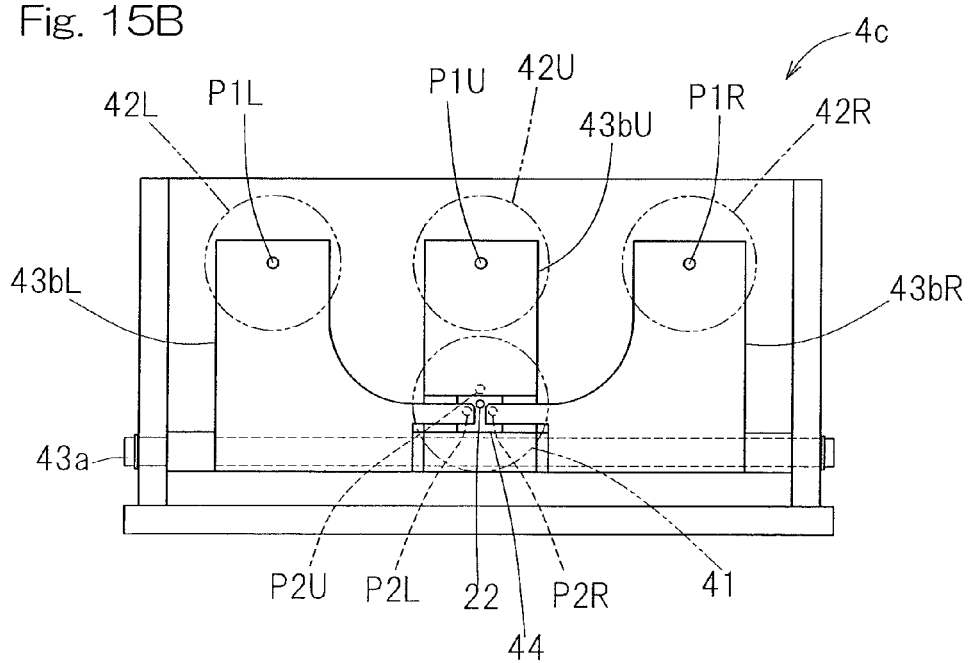
FIG. 15B is a cross sectional view taken along the line XVB-XVB in FIG. 15A.

FIGS. 15A and 15B illustrate the tool rotation drive mechanism 4b and the attitude altering drive mechanism 4c both employed in this remote controlled actuator. The tool rotation drive mechanism 4b is of a structure identical with that shown in FIGS. 3A and 3B. The attitude altering drive mechanism 4c, shown in FIG. 15A, makes use of respective attitude altering drive sources 42 (42U, 42L, 42R) that are associated, respectively, with the attitude altering members 31 (31U, 31L, 31R). The movement of the output rod 42a of the attitude altering drive sources 42 is transmitted to the corresponding attitude altering member 31 through a force increasing and transmitting mechanism 43. The force increasing and transmitting mechanism 43 includes pivot levers 43b (43bU, 43bL, 43bR) pivotable about a support pin 43a. The attitude altering drive mechanism 4c is provided with operating amount detectors 45 (45U, 45L, 45R) for detecting the operating amount of the corresponding attitude altering drive sources 42 (42U, 42L, 42R) independent of each other, and also, is provided with supply power meters 47 (47U, 47L, 47R) for detecting the electric energy supplied to the corresponding attitude altering drive sources 42 (42U, 42L, 42R), which are electrically operated actuators, independent of each other.

During operation, the respective attitude altering drive sources 42 (42U, 42L, 42R) are driven for the cooperative advancement and retraction of the respective attitude altering members 31 (31U, 31L, 31R) such as shown in FIG. 2B, to drive the distal end member 2 to alter the attitude thereof. By way of example, when one of the attitude altering members 31U, shown in FIG. 14B, is advanced towards the distal, tip end side while the other two attitude altering members 31L and 31R are retracted, the housing 11 for the distal end member 2 is pressed by the upper attitude altering member 31U to allow the distal end member 2 to be altered in attitude along the guide surfaces F1 and F2 with the distal, tip end side consequently oriented downwardly as viewed in FIG. 14A. At this time, those attitude altering drive sources 42 are controlled so that the amount of advance or retraction of each of the attitude altering members 31 may become proper. On the other hand, when each of those attitude altering members 31 is retracted or advanced, the housing 11 for the distal end member 2 is pressed by the attitude altering members 31L and 31R, which are shown on lower left and lower right sides, and, consequently, the distal end member 2 is altered in attitude along the guide surfaces F1 and F2 with the tip end side oriented upwardly as viewed in FIG. 14A.

Also, when while the attitude altering member 31U on the upper side shown in FIG. 14A is held still, the attitude altering member 31L on the left side is advanced towards the tip end side and the attitude altering member 31R on the right side is retracted, the housing 11 for the distal end member 2 is pressed by the attitude altering member 31L on the left side to allow the distal end member 2 to be oriented rightwards, that is, to be altered in attitude along the guide surfaces F1 and F2 with the distal end member 2 oriented towards a rear side of the sheet of the drawing of FIG. 14A. Conversely, when the attitude altering members 31L and 31R on the left and right sides are advanced and retracted, the housing 11 for the distal end member 2 is pressed by the attitude altering member 31R on the right side, allowing the distal end member 2 to be altered in attitude so that the distal end member 2 can be guided along the guide surfaces F1 and F2 so as to be oriented leftwards.

The use of the attitude altering members 31 at the three circumferential locations as hereinabove described is effective to allow the distal end member 2 to be altered in attitude in two axis directions (X-axis and Y-axis directions) upwardly or downwardly and leftwards or rightwards. At this time, respective pressures from the three attitude altering members 31 and the reactive force from the constraint member 21 act on the distal end member connecting unit 15 and, therefore, the attitude of the distal end member 2 is determined in dependence on the balance of those working forces. According to the above described construction, since the housing 11 for the distal end member 2 is pressed by the three attitude altering members 31, the attitude stability of the distal end member 2 can be further increased.

As described hereinabove, where the attitude altering member 31 is provided at those three circumferential locations, the attitude altering drive mechanism 4c can be structured as shown in, for example, 15B. In other words, three attitude altering drive sources 42 (42U, 42L, 42R) for individually advancing and retracting the respective attitude altering members 31 (31U, 31L, 31R) are arranged on left and right sides in parallel relation to each other; pivotable levers 43b (43bU, 43bL, 43bR) operatively associated with the respective attitude altering drive sources 42 are provided for pivotal movement about a common support pin 43a; a force of the output rod 42a of each attitude altering drive source 42 acts on a working point P1 (P1U, P1L, P1R) on the respective pivot lever 43b, which is spaced a long distance from the common support pin 43a; and a force can be applied to the attitude altering member 31 at a force point P2 (P2U, P2L, P2R) which is spaced a short distance from the common support pin 43a. Thereby, the output of each of the attitude altering drive sources 42 can, after having been increased, be transmitted to the associated attitude altering member 31. It is to be noted that the rotary shaft 22 is allowed to pass through an opening 44 defined in the pivot lever 43bU for the upper attitude altering member 31U.

With particular reference to FIGS. 16A and 16B, a tenth preferred embodiment of the present invention will be described in detail. In the spindle guide section 3 employed in the remote controlled actuator according to this tenth embodiment, as shown in FIG. 16B, a hollow 24 of the outer shell pipe 25 is made up of a round hole 24a at a center thereof and three grooved portions 24b recessed radially outwardly from respective circumferential positions on the outer periphery of the round hole 24a spaced 120° in phase from each other. A peripheral wall of a tip end of each of the grooved portions 24b represents a semicircular sectional shape. The round hole 24a accommodates therein the rotary shaft 22 and the rolling bearings 26, and the attitude altering members 31 (31U, 31L, 31R) are accommodated respectively within the grooved portions 24b.

Since the outer shell pipe 25 is so designed as to have the specific sectional shape as hereinbefore described, the wall thickness t of the remaining portion of the outer shell pipe 25 other than that where the grooved portions 24b are increased, resulting in an increase of the moment of inertia of area of the outer shell pipe 25. In other words, the rigidity of the spindle guide section 3 is increased. Accordingly, not only can the positioning accuracy of the distal end member 2 be enhanced, but the cutting capability can also be improved. Also, the positioning of the guide pipes 30 in the respective grooved portions 24b makes it easy to position the guide pipes 30 in the circumferential direction, resulting in a good assemblability. It is to be noted that although in describing the foregoing various embodiments of the present invention, a fixing and support member has been shown and described as comprised of the guide pipes 30 and the reinforcement shafts 34, the fixing and support member employed in the practice of this embodiment is only the guide pipes 30.

FIGS. 17A to 17C illustrate an eleventh preferred embodiment of the present invention, reference to which will be hereinafter made for the discussion of such embodiment. The remote controlled actuator according to this fifth embodiment is such that the base end face 11b (FIG. 17C) of the housing 11 for the distal end member 2, shown in FIG. 17A, is formed with a radial groove portion 11c and the spherical tip end of the attitude altering member 31 is held in contact with a bottom face of the radial groove portion 11c. This radial groove portion 11c cooperates with the attitude altering member 31 to form a rotation preventing mechanism 37 and, accordingly, when the tip end portion of the attitude altering member 31, then inserted into the radial groove portion 11c, contacts a side face of the radial groove portion 11c, the distal end member 2 can be prevented from rotating about the center line CL of the spindle 13 relative to the spindle guide section 3.

Such a rotation preventing mechanism 37 will prevent, even when the distal end member 2 holding the tool 1 becomes out of control due to, for example, a failure in the attitude altering drive mechanism 4c (FIG. 3A) or a controller for the mechanism 4c, rotation of the distal end member 2 about the center line CL that may unintentionally damage the vicinity of the location to be worked and prevent the fracture in the distal end member 2 itself. It should be noted that FIG. 17B shows an example in which the remote controlled actuator includes a single attitude altering member 31, but the above discussion equally applies to cases in which the remote controlled actuator includes a plurality of attitude altering members 31.

A twelfth preferred embodiment of the present invention will be hereinafter described with particular reference to FIGS. 18A to 18C. Those figures corresponds to FIGS. 2A to 2C referred to in connection with the previously described first embodiment and, therefore, component parts similar to those employed in the first embodiment are designated by like reference numerals and the details thereof are not reiterated for the sake of brevity. This twelfth embodiment is such that the rolling bearings 26, which are the rotary shaft support members, are supported by the guide pipe 30 and the reinforcement shafts 34, which are the fixing and supporting member, in a fixed condition and, accordingly, vibration of the rotary shaft 22 can be suppressed. For this reason, not only can impairment to the rotary shaft 22 and the rolling bearings 26 be prevented, but also vibrations and noises occurring during the use can be reduced.

Also, as shown in FIG. 18B, the use is made of a guide pipe restraining unit 50G, comprised of a gap adjusting member for adjusting a gap dimension between the rotary shaft support members 26 and the fixing and supporting member 30, 34. For the gap adjusting member, an elastic member 52 is employed. Accordingly, the difference in gap dimension 6 resulting from the manufacturing accuracy can be accommodated and the rolling bearings 26 can be assuredly supported by the guide pipe 30 and the reinforcement shafts 34 in the fixed condition.

Because of the provision of the elastic member 52, it resiliently deforms in correspondence therewith regardless of the shape of the spindle guide section 3, thereby allowing the guide pipe 30 and the reinforcement shafts 34 to support the rolling bearings 26 assuredly in the fixed condition. By way of example, where such a gap adjusting member as the elastic member 52 is not provided, the following problems may arise. In the case of the spindle guide section 3 being of the linear shape as shown in FIG. 1A, if the gap 51 between the rolling bearings 26 and both of the guide pipe 30 and the reinforcement shafts 34 as shown in FIG. 5 is too large, the rolling bearings 26 cannot be firmly supported by the guide pipe 30 and the reinforcement shafts 34 and, therefore, vibration of the rotary shaft 22 will become considerable. In the case of the spindle guide section 3 having the curved shape as shown in FIG. 1B, if the gap 51 shown in FIG. 5 is too small, the assemblability will become worse. Hence, the provision of the elastic member 52 is effective to resolve such problems as discussed above.

Also, since the guide pipe 30, which is a member for defining the guide hole 30a, is rendered to concurrently serve as the fixing and supporting member, the number of component parts can be reduced.

Figure 19:
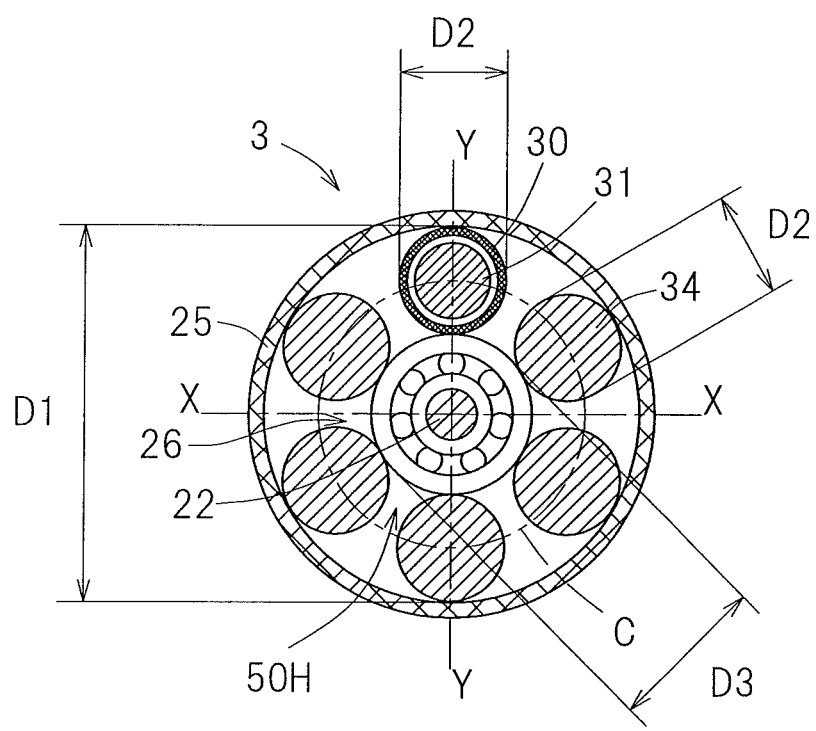
FIG. 19 is a sectional view showing the spindle guide section employed in the remote controlled actuator according to a thirteenth preferred embodiment of the present invention.

Referring now to FIG. 19, a thirteenth preferred embodiment of the present invention will be described. In this thirteenth embodiment, no elastic member such as employed in the practice of the twelfth embodiment described previously is employed and, as a gap adjusting unit 50H in place of the gap adjusting member, adjustment is made of at least one or more of the inner diametric dimension D1 of the outer shell pipe 25, the outer diametric dimension D2 of the guide pipe 30 and the reinforcement shaft 34 and the outer diametric dimension D3 of each rolling bearing 26 to thereby adjust the gap dimension between each rolling bearing 26 and both of the guide pipe 30 and the reinforcement shafts 34. In this case, the gap 51 is preferably within the range of, for example, +30 μm to −10 μm. Although ideally it must be a negative gap, it may occur that it must be a positive gap, considering the assemblability in the case of the spindle guide section 3 of the curved shape.

For example, where the inner diametric dimension D1 of the outer shell pipe 25 and the outer diametric dimension D3 of each of the rolling bearings 26 are machined or otherwise processed highly accurately, a plurality of guide pipes 30 and reinforcement shafts 34 of varying outer diametric dimensions D2 are prepared for, and one of the guide pipes 30 and the reinforcement shafts 34 which suit to the shape of the spindle guide section 3 is selected so that the gap dimension 6 can be adjusted. Where the inner diametric dimension D1 of the outer shell pipe 25 and the outer diametric dimension D2 of both of the guide pipe 30 and the reinforcement shaft 34 are highly accurately machined or otherwise processed, a plurality of rolling bearings 26 of varying outer diametric dimensions D3 are prepared for, or alternatively, where the outer diametric dimension D2 of the guide pipe 25 and the outer diametric dimension D3 of each rolling bearing 26 are highly accurately machined or otherwise processed, a plurality of outer shell pipe 25 of varying inner diametric dimensions D1 are prepared for. Thus, the gap dimension 6 can be adjusted in a manner similar to that described previously.

In general, if the gap dimension between both of the guide pipe 30 and the reinforcement shaft 34 and each of the rolling bearings 26 is too large, vibration of the rotary shaft 22 becomes considerable. For this reason, although it is preferred that the gap dimension is as small as possible, in the event of the spindle guide section 3 of the curved shape, the assemblability will be adversely affected if a certain gap dimension is not available. Where the spindle guide section 3 used is of the linear shape or a shape approximating to the linear shape, the gap 51 can be rendered a negative gap. Although the use of the negative gap makes it possible to fix the rolling bearings 26 firmly, the use of an extreme negative gap may result in reduction of the assemblability. From a series of experiments conducted, it has been ascertained that the gap dimension is preferably within the range of +100 μm to −10 μm.

Although in any one of the foregoing embodiments of the present invention, the rotary shaft supporting member has been shown and described as constituted by each rolling bearing 26, the rotary shaft support member may be a slide bearing or any other member capable of rotatably supporting the rotary shaft 22.

Although the present invention has been fully described as applied to the remote controlled actuator for medical use, the present invention can be equally applied to the remote controlled actuator for any other use than the medical use. By way of example, if it is designed for use in machine processing, drilling to form a curved hole and cutting at a site deep into the groove can be accomplished.

Any one of the various embodiments of the present invention hereinbefore fully described encompasses any one of the following modes 1 to 11 which do not require the use of the guide pipe 30 having the guide hole 30a, the guide pipe 30 being provided for by the present invention.

[Mode 1]

The remote controlled actuator according to the mode 1 includes a spindle guide section of an elongated configuration, a distal end member fitted to a tip end of the spindle guide section through a distal end member connecting unit for alteration in attitude, and a drive unit housing to which a base end of the spindle guide section is connected;

in which the distal end member rotatably supports a spindle for holding a tool;

in which the spindle guide section includes a rotary shaft for transmitting rotation of a tool rotating drive source, provided within the drive unit housing, to the spindle, a guide hole so as to extend to opposite ends thereof, and an attitude altering member reciprocally movably inserted within the guide hole for altering the attitude of the distal end member;

in which the attitude altering member is, while a tip end thereof is held in contact with the distal end member, selectively advanced or retracted one at a time;

in which an attitude altering drive source for selectively advancing or retracting the attitude altering member is provided within the drive unit housing; and in which a rotary shaft support member for rotatably supporting the rotary shaft within the spindle guide section, a fixing and supporting member for supporting the rotary shaft support member in a fixed condition, and a gap adjusting unit for adjusting a gap dimension between the rotary shaft support member and the fixing and supporting member are provided.

According to the above described construction, as a result of rotation of the tool fitted to the distal end member, cutting of the bone or the like takes place. In such case, when the attitude altering member is selectively advanced and retracted one at a time by the attitude altering drive source, the tip end of the attitude altering member works on the distal end member to allow the attitude of the distal end member, fitted to the tip end of the spindle guide section through the distal end member connecting unit for alteration in attitude, to alter. The attitude altering drive source is provided within the drive unit housing on the base end side of the spindle guide section and the alteration of the attitude of the distal end member is carried out by remote control. Since the attitude altering member is passed through the guide hole, the attitude altering member can work on the distal end member properly at all time without being displaced in a direction transverse to the longitudinal direction thereof, and the operation to alter the attitude of the distal end member takes place accurately.

According to the above construction, since the use is made of the rotary shaft support member for rotatably supporting the rotary shaft within the spindle guide section, the rotation of the tool rotation drive source can be transmitted to the spindle by driving the rotary shaft at a high speed. For this reason, the processing can be performed with the tool driven at a high speed and the surface to be cut can be finished beautifully. Since the rotary shaft support member is supported in the fixed condition by the fixing and supporting member, vibration of the rotary shaft can be suppressed and an undesirable impairment to the rotary shaft and/or the rotary shaft support member can be avoided. Also, since the vibration of the actuator in its entirety can be minimized during the use, the operability thereof increases and the noise is reduced.

Since the use is made of the gap adjusting member for adjusting the gap dimension between the rotary shaft support member and the fixing and supporting member, it can accommodate the difference in gap dimension resulting from the manufacturing accuracy or the like and the rotary shaft support member can be assuredly supported by the fixing and supporting member in the fixed condition. Also, whatever shape the spindle guide section may take, the rotary shaft support member can be assuredly supported by the fixing and supporting member in the fixed condition to suit thereto and, hence, an excellent assemblability and an excellent mass-productivity can be obtained. By way of example, where no gap adjusting unit is employed, in the case of the spindle guide section of the linear shape, the large gap dimension between the rotary shaft support member and the fixing and supporting member prevents the fixing and supporting member from firmly supporting the rotary shaft support member, and thus, vibration of the rotary shaft is considerable. As a result, it may occur that the rotary shaft and/or the rotary shaft support member may be damaged and vibration and noise during the use will become considerable. In the case of the spindle guide section of the curved shape, the assemblability will be adversely affected if the gap is small. The use of the gap adjusting unit is effective to resolve those problems as discussed above. The rolling bearings are suited for rotatably supporting the rotary shaft. If the spring element for applying a preload to the neighboring rolling bearings is employed between the neighboring rolling bearings functioning as the rotary shaft support members, the support rigidity of the rolling bearing is high, and as a result, the rotary shaft can be driven at a high speed.

[Mode 2]
In the mode 1 described, above, the fixing and supporting member may have the guide hole in an inner diametric portion thereof.

[Mode 3]
In the mode 1 described above, the rotary shaft support member is a plurality of rolling bearings arranged in an axial direction and a spring element for applying a preload to the rolling bearings may be provided between the neighboring rolling bearings.

[Mode 4]
In the mode 1 described above, the gap adjusting unit may be an elastic member provided on an outer periphery of the rotary shaft support member.

[Mode 5]
In the mode 4 described above, the rotary shaft support member is a rolling bearing having an outer ring with at least one or more annular groove provided in an outer diametric surface of the outer ring and the elastic member as the gap adjusting unit may be an O-ring engaged in the annular groove.

[Mode 6]
In the mode 5 described above, two or more annular grooves are provided in an outer diametric surface of an outer ring of the rolling bearing and the elastic member as the gap adjusting unit may be an O-ring engaged in each of the two or more annular grooves.

[Mode 7]
In the mode 4 described above, the elastic member as the gap adjusting unit may be a coating formed on an outer peripheral surface of the rotary shaft support member.

[Mode 8]
In the mode 4 described above, the elastic member as the gap adjusting unit may be in a compressed condition when the spindle guide section is in an assembled condition.

[Mode 9]
In the mode 1 described above, where it includes an outer shell pipe forming an outer shell for the spindle guide section and a guide pipe positioned within the outer shell pipe and having the guide hole formed therein, the gap adjusting unit may be of a structure in which the gap dimension is adjusted by adjusting at least one or more of an inner diametric dimension of the outer shell pipe, an outer diametric dimension of the guide pipe and an outer diametric dimension of the rotary shaft support member.

[Mode 10]
In the mode 1 described above, the gap dimension is preferably within the range of +100 $\mu$m to −10 $\mu$m.

[Mode 11]
In the mode 1 described above, the spindle guide section may have a curved portion.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

REFERENCE NUMERALS

1 . . . Tool
2 . . . Distal end member
3 . . . Spindle guide section 4a . . . Drive unit housing
5 . . . Controller
13 . . . Spindle
15 . . . Distal end member coupling unit
22 . . . Rotary shaft
25 . . . Outer shell pipe
26 . . . Rolling bearing (Rotary shaft support member)
30 . . . Guide pipe (Fixing and supporting member)
30a . . . Guide hole
31 . . . Attitude altering member
34 . . . Reinforcement shaft (Fixing and supporting member)
41 . . . Tool rotation drive source
42 . . . Attitude altering drive source
50 to 50H . . . Guide pipe restraining unit
51 . . . Gap
52 . . . Elastic member (Gap adjusting member)
55 . . . Guide pipe contact member
57 . . . Hole (Compressive force applying unit)
58 . . . Flange member
59 . . . Groove (Compressive force applying unit)
72 . . . Solder deposit
73 . . . Weld deposit

What is claimed is:

1. A remote controlled actuator which comprises a spindle guide section of an elongated configuration, a distal end member fitted to a tip end of the spindle guide section through a distal end member connecting unit for alteration in attitude, and a drive unit housing to which a base end of the spindle guide section is connected;
    in which the distal end member rotatably supports a spindle for holding a tool;
    in which the spindle guide section includes a rotary shaft for transmitting rotation of a tool rotating drive source, provided within the drive unit housing, to the spindle, a guide hole so as to extend to opposite ends thereof, and an attitude altering member reciprocally movably inserted within the guide hole for altering the attitude of the distal end member;
    in which the attitude altering member is, while a tip end thereof is held in contact with the distal end member, selectively advanced or retracted one at a time;
    in which an attitude altering drive source for selectively advancing or retracting the attitude altering member is provided within the drive unit housing; and
    further comprising an outer shell pipe defining an outer shell for the spindle guide section, a guide pipe positioned within the outer shell pipe having an inner diametric hole defining the guide hole, and a guide pipe restraining unit for restraining the guide pipe from moving within the outer shell pipe.

2. The remote controlled actuator as claimed in claim 1, in which the guide pipe restraining unit is operable to urge the guide pipe against an inner diametric surface of the outer shell pipe.

3. The remote controlled actuator as claimed in claim 2, further comprising a rotary shaft support member for rotatably supporting the rotary shaft and
    in which the guide pipe restraining unit is operable to urge the guide pipe against the inner diametric surface of the outer shell pipe by adjusting at least one or more of an inner diametric dimension of the outer shell pipe, an outer diametric dimension of the guide pipe and an outer diametric dimension of the rotary shaft support member.

4. The remote controlled actuator as claimed in claim 2, in which the rotary shaft is positioned at a center of the outer shell pipe,
    in which a plurality of the guide pipe or at least one guide pipe and an arbitrarily chosen number of identical outer diametric members each having an outer diameter, which is the same as that of the guide pipe, are arranged in a circumferential direction in a juxtaposed fashion relative to each other, and
    in which, when an inner diametric dimension of the outer shell pipe is expressed by D1, an outer diametric dimension of the identical outer diametric member and the guide pipe is expressed by D2, and an outer diametric dimension of the rotary shaft support member is expressed by D3, such a relationship as $D1 \leq D2 \times 2 + D3$ establishes.

5. The remote controlled actuator as claimed in claim 1, further comprising a plurality of rotary shaft support members for rotatably supporting the rotary shaft and
    in which the guide pipe restraining unit includes a guide pipe contact member provided between at least one set of the neighboring rotary shaft support members to contact the guide pipe.

6. The remote controlled actuator as claimed in claim 5, in which the guide pipe contact member functions to urge the guide pipe against an inner diametric surface of the outer shell pipe.

7. The remote controlled actuator as claimed in claim 5, in which each of the rotary shaft support members is a rolling bearing and
    further comprising a spring element provided between the neighboring rolling bearings for applying a preload to the neighboring rolling bearings and
    in which the guide pipe contact member is provided at an axial location where the spring element is disposed on a side of an inner ring of each of the rolling bearings.

8. The remote controlled actuator as claimed in claim 1, further comprising a rotary shaft support member for rotatably supporting the rotary shaft within the spindle guide section, and a fixing and supporting member for supporting the rotary shaft support member in a fixed condition, and
    in which the guide pipe restraining unit comprises a gap adjusting member for adjusting a gap dimension between the rotary shaft support member and the fixing and supporting member.

9. The remote controlled actuator as claimed in claim 8, in which the gap adjusting member comprises an elastic member provided on an outer periphery of the rotary shaft support member.

10. The remote controlled actuator as claimed in claim 9, in which the rotary shaft support member is a rolling bearing including an outer ring having an outer diametric surface provided with one or more annular groove and in which the elastic member as the gap adjusting member comprises an O-ring engaged in the annular groove.

11. The remote controlled actuator as claimed in claim 9, in which the elastic member as the gap adjusting unit is coated on an outer peripheral surface of the rotary shaft support member.

12. The remote controlled actuator as claimed in claim 8, in which the gap dimension is within the range of +100 μm to −10 μm.

* * * * *